(12) United States Patent
Lee et al.

(10) Patent No.: US 10,300,276 B2
(45) Date of Patent: May 28, 2019

(54) COCHLEAR IMPLANTS HAVING MRI-COMPATIBLE MAGNET APPARATUS AND ASSOCIATED METHODS

(71) Applicants: ADVANCED BIONICS AG, Staefa (CH); James George Elcoate Smith, Santa Clarita, CA (US)

(72) Inventors: Sung Jin Lee, Valencia, CA (US); James George Elcoate Smith, Santa Clarita, CA (US)

(73) Assignee: Advanced Bionics AG, Staefa (CH)

( * ) Notice: Subject to any disclaimer, the term of this patent is extended or adjusted under 35 U.S.C. 154(b) by 0 days.

(21) Appl. No.: 15/568,470

(22) PCT Filed: May 24, 2016

(86) PCT No.: PCT/US2016/033944
§ 371 (c)(1),
(2) Date: Oct. 21, 2017

(87) PCT Pub. No.: WO2016/191429
PCT Pub. Date: Dec. 1, 2016

(65) Prior Publication Data
US 2018/0110986 A1 Apr. 26, 2018

Related U.S. Application Data

(63) Continuation-in-part of application No. PCT/US2015/033040, filed on May 28, 2015.

(51) Int. Cl.
*A61N 1/375* (2006.01)
*A61N 1/36* (2006.01)
(Continued)

(52) U.S. Cl.
CPC ....... *A61N 1/36038* (2017.08); *A61N 1/0541* (2013.01); *A61N 1/086* (2017.08);
(Continued)

(58) Field of Classification Search
CPC .... A61N 1/36038; A61N 1/086; A61N 1/372; A61N 1/3758; A61N 1/375
See application file for complete search history.

(56) References Cited

U.S. PATENT DOCUMENTS

| 4,352,960 A | 10/1982 | Dormer et al. |
| 4,595,390 A | 6/1986 | Hakim et al. |

(Continued)

FOREIGN PATENT DOCUMENTS

| EP | 2117489 B1 | 5/2010 |
| EP | 2853287 A1 | 4/2015 |

(Continued)

OTHER PUBLICATIONS

PCT International Search and Written Opinion dated Oct. 18, 2016 for PCT App. Ser. No. PCT/US2016/033944.
(Continued)

*Primary Examiner* — Kennedy Schaetzle
(74) *Attorney, Agent, or Firm* — Henricks Slavin LLP

(57) ABSTRACT

A cochlear implant is disclosed including a cochlear lead, an antenna, a stimulation processor, a magnet apparatus, associated with the antenna, including a case, a divider, and a plurality of magnetic material particles that are movable relative to one another within sub-volumes defined by the divider.

15 Claims, 17 Drawing Sheets

(51) Int. Cl.
*A61N 1/372* (2006.01)
*A61N 1/08* (2006.01)
*A61N 1/05* (2006.01)

(52) U.S. Cl.
CPC ......... *A61N 1/36036* (2017.08); *A61N 1/375* (2013.01); *A61N 1/37229* (2013.01); *A61N 1/08* (2013.01); *H04R 2225/67* (2013.01)

(56) References Cited

U.S. PATENT DOCUMENTS

| | | | |
|---|---|---|---|
| 4,606,329 | A | 8/1986 | Hough |
| 4,618,949 | A | 10/1986 | Lister |
| RE32,947 | E | 6/1989 | Dormer et al. |
| 5,290,281 | A | 3/1994 | Tschakaloff |
| 5,755,762 | A | 5/1998 | Bush |
| 5,824,022 | A | 10/1998 | Zilberman et al. |
| 5,945,762 | A | 8/1999 | Chen et al. |
| 6,178,353 | B1 * | 1/2001 | Griffith .............. A61N 1/37223 607/61 |
| 6,190,305 | B1 | 2/2001 | Ball et al. |
| 6,217,508 | B1 | 4/2001 | Ball et al. |
| 6,292,678 | B1 | 9/2001 | Hall et al. |
| 6,348,070 | B1 | 2/2002 | Teissl et al. |
| 6,358,281 | B1 | 3/2002 | Berrang et al. |
| 6,838,963 | B2 | 1/2005 | Zimmerling |
| 7,091,806 | B2 | 8/2006 | Zimmerling et al. |
| 7,190,247 | B2 | 3/2007 | Zimmerling |
| 7,566,296 | B2 | 7/2009 | Zimmerling et al. |
| 7,609,061 | B2 | 10/2009 | Hochmair |
| 7,642,887 | B2 | 1/2010 | Zimmerling |
| 7,680,525 | B1 | 3/2010 | Damadian |
| 7,774,069 | B2 | 8/2010 | Olson et al. |
| 7,856,986 | B2 | 12/2010 | Darley |
| 7,881,800 | B2 | 2/2011 | Daly et al. |
| 7,976,453 | B2 | 7/2011 | Zimmerling et al. |
| 8,013,699 | B2 | 9/2011 | Zimmerling |
| 8,118,725 | B2 | 2/2012 | Zimmerling et al. |
| 8,255,058 | B2 | 8/2012 | Gibson et al. |
| 8,340,774 | B2 | 12/2012 | Hochmair et al. |
| 8,634,909 | B2 | 1/2014 | Zimmerling et al. |
| 8,733,494 | B1 | 5/2014 | Leigh |
| 8,734,475 | B2 | 5/2014 | Ekvall et al. |
| 8,744,106 | B2 | 6/2014 | Ball |
| 8,758,394 | B2 | 6/2014 | Zimmerling et al. |
| 8,787,608 | B2 | 7/2014 | Van Himbeeck et al. |
| 8,790,409 | B2 | 7/2014 | Van den Heuvel et al. |
| 8,825,171 | B1 | 9/2014 | Thenuwara et al. |
| 8,897,475 | B2 | 11/2014 | Ball et al. |
| RE45,701 | E | 9/2015 | Zimmerling et al. |
| 9,126,010 | B2 | 9/2015 | Shah et al. |
| 9,162,054 | B2 | 10/2015 | Dalton |
| 9,227,064 | B2 | 1/2016 | Duftner |
| 9,295,425 | B2 | 3/2016 | Ball |
| 9,314,625 | B2 | 4/2016 | Kasic, II et al. |
| 9,352,149 | B2 | 5/2016 | Thenuwara et al. |
| RE46,057 | E | 7/2016 | Zimmerling et al. |
| 9,392,382 | B2 | 7/2016 | Nagl et al. |
| 9,420,388 | B2 | 8/2016 | Ball |
| 9,549,267 | B2 | 1/2017 | Nagl et al. |
| 9,615,181 | B2 | 4/2017 | Nagl et al. |
| 9,656,065 | B2 | 5/2017 | Tourrel et al. |
| 9,919,154 | B2 | 3/2018 | Lee |
| 9,931,501 | B2 | 4/2018 | Smyth |
| 2004/0012470 | A1 * | 1/2004 | Zimmerling ............. A61N 1/37 335/207 |
| 2004/0260362 | A1 | 12/2004 | Darley |
| 2005/0001703 | A1 | 1/2005 | Zimmerling |
| 2005/0004629 | A1 | 1/2005 | Gibson et al. |
| 2005/0062567 | A1 | 3/2005 | Zimmerling et al. |
| 2006/0244560 | A1 | 11/2006 | Zimmerling et al. |
| 2007/0053536 | A1 | 3/2007 | Westerkull |
| 2007/0126540 | A1 | 6/2007 | Zimmerling |
| 2008/0103350 | A1 | 5/2008 | Farone |
| 2008/0195178 | A1 | 8/2008 | Kuzma |
| 2009/0048580 | A1 | 2/2009 | Gibson |
| 2009/0099403 | A1 | 4/2009 | Zimmerling et al. |
| 2009/0134721 | A1 | 5/2009 | Zimmerling |
| 2009/0248155 | A1 | 10/2009 | Parker |
| 2009/0287278 | A1 | 11/2009 | Charvin |
| 2010/0004716 | A1 | 1/2010 | Zimmerling et al. |
| 2010/0046778 | A1 | 2/2010 | Crawford et al. |
| 2010/0046779 | A1 | 2/2010 | Crawford et al. |
| 2011/0009925 | A1 | 1/2011 | Leigh et al. |
| 2011/0022120 | A1 * | 1/2011 | Ball ........................ A61N 1/08 607/57 |
| 2011/0218605 | A1 | 9/2011 | Cryer |
| 2011/0224756 | A1 | 9/2011 | Zimmerling et al. |
| 2011/0255731 | A1 | 10/2011 | Ball |
| 2011/0264172 | A1 | 10/2011 | Zimmerling et al. |
| 2013/0079749 | A1 | 3/2013 | Overstreet et al. |
| 2013/0184804 | A1 | 7/2013 | Dalton |
| 2013/0343588 | A1 | 12/2013 | Karunasiri |
| 2014/0012069 | A1 | 1/2014 | Ball |
| 2014/0012070 | A1 | 1/2014 | Nagl et al. |
| 2014/0012071 | A1 | 1/2014 | Nagl et al. |
| 2014/0012349 | A1 | 1/2014 | Zimmerling |
| 2014/0121449 | A1 | 5/2014 | Kasic et al. |
| 2014/0121586 | A1 | 5/2014 | Bertrand et al. |
| 2014/0163692 | A1 | 6/2014 | Van den Heuvel et al. |
| 2014/0343626 | A1 | 11/2014 | Thenuwara et al. |
| 2015/0025613 | A1 | 1/2015 | Nyberg, II et al. |
| 2015/0073205 | A1 | 3/2015 | Ball et al. |
| 2015/0087892 | A1 | 3/2015 | Tourrel et al. |
| 2015/0100109 | A1 | 4/2015 | Feldman et al. |
| 2015/0265842 | A1 | 9/2015 | Ridker |
| 2015/0367126 | A1 | 12/2015 | Smyth |
| 2015/0382114 | A1 | 12/2015 | Andersson et al. |
| 2016/0037273 | A1 | 2/2016 | Gustafsson |
| 2016/0144170 | A1 | 5/2016 | Gibson et al. |
| 2016/0205484 | A1 | 7/2016 | Nagl et al. |
| 2016/0310737 | A1 | 10/2016 | Tourrel et al. |
| 2016/0361537 | A1 | 12/2016 | Leigh et al. |
| 2016/0381473 | A1 | 12/2016 | Gustafsson |
| 2016/0381474 | A1 | 12/2016 | Gustafsson et al. |
| 2017/0050027 | A1 | 2/2017 | Andersson et al. |
| 2017/0078808 | A1 | 3/2017 | Kennes |
| 2017/0239476 | A1 | 8/2017 | Lee et al. |
| 2018/0028818 | A1 | 2/2018 | Anderson et al. |
| 2018/0110985 | A1 | 4/2018 | Walter |
| 2018/0133486 | A1 | 5/2018 | Smith |
| 2018/0185634 | A1 | 7/2018 | Smyth |
| 2018/0296826 | A1 | 10/2018 | Lee et al. |
| 2018/0304078 | A1 | 10/2018 | Crawford et al. |
| 2018/0369586 | A1 | 12/2018 | Lee et al. |
| 2019/0046797 | A1 | 2/2019 | Calixto et al. |

FOREIGN PATENT DOCUMENTS

| | | |
|---|---|---|
| EP | 2560730 B1 | 11/2016 |
| EP | 3138605 A1 | 3/2017 |
| EP | 2098198 B1 | 9/2017 |
| WO | WO9858990 A1 | 12/1998 |
| WO | WO03081976 A2 | 10/2003 |
| WO | WO03092326 A1 | 11/2003 |
| WO | WO2004014269 A1 | 2/2004 |
| WO | WO2004014270 A1 | 2/2004 |
| WO | WO2007024657 A2 | 3/2007 |
| WO | WO2009124045 A1 | 10/2009 |
| WO | WO2009124174 A2 | 10/2009 |
| WO | WO2009149069 A2 | 12/2009 |
| WO | WO2010000027 A1 | 1/2010 |
| WO | WO2010083554 A1 | 7/2010 |
| WO | WO2011011409 A1 | 1/2011 |
| WO | WO2011109486 A2 | 9/2011 |
| WO | WO2011133747 A1 | 10/2011 |
| WO | WO2013043176 A1 | 3/2013 |
| WO | WO2013063355 A1 | 5/2013 |
| WO | WO2014011441 A1 | 1/2014 |
| WO | WO2014011582 A2 | 1/2014 |
| WO | WO2014046662 A1 | 3/2014 |
| WO | WO2014164023 A1 | 10/2014 |
| WO | WO2015065442 A1 | 5/2015 |
| WO | WO2016016821 A1 | 2/2016 |

(56) References Cited

FOREIGN PATENT DOCUMENTS

| WO | WO2016190886 A1 | 12/2016 |
|---|---|---|
| WO | WO2016207856 A1 | 12/2016 |
| WO | WO2017027045 A1 | 2/2017 |
| WO | WO2017027046 A1 | 2/2017 |
| WO | WO2017029615 A1 | 2/2017 |
| WO | WO2017034530 A1 | 3/2017 |
| WO | WO2017046650 A1 | 3/2017 |
| WO | WO2017087004 A1 | 5/2017 |
| WO | WO2017105510 A1 | 6/2017 |
| WO | WO2017105511 A1 | 6/2017 |
| WO | WO2017105604 A1 | 6/2017 |
| WO | WO2017172566 A1 | 10/2017 |
| WO | WO2018190813 A1 | 10/2018 |
| WO | WO2018191314 A1 | 10/2018 |
| WO | WO2018199936 A1 | 11/2018 |

OTHER PUBLICATIONS

Ju Hyun Jeon et al., "Reversing the Polarity of a Cochlear Implant Magnet After Magnetic Resonance Imaging," Auris Nasus Larynx, vol. 39, No. 4, pp. 415-417, Aug. 1, 2012.

Teissl et al., "Magentic Resonance Imaging and Cochlear Implants: Compatibility and Safety Aspects," Journal of Magnetic Resonance Imaging, Society For Magnetic Resonance Imaging, vol. 9, No. 1, pp. 26-38, Jan. 1, 1999.

U.S. Appl. No. 15/568,469 filed Oct. 21, 2017 U.S. Pat. No. 20180110985A1.

U.S. Appl. No. 15/770,207 filed Apr. 22, 2018 U.S. Pat. No. 20180304078 A1.

U.S. Appl. No. 16/060,383 filed Jun. 7, 2018 U.S. Pat. No. 20180369586 A1.

U.S. Appl. No. 15/591,054 filed May 9, 2017 U.S. Pat. No. 9919154.

U.S. Appl. No. 16/009,600 filed Jun. 15, 2018 U.S. Pat. No. 20180296826A1.

U.S. Appl. No. 15/568,470 filed Oct. 21, 2017 U.S. Pat. No. 20180110986A1.

U.S. Appl. No. 16/101,390 filed Aug. 10, 2018 U.S. Pat. No. 20190046797 A1.

U.S. Appl. No. 15/703,808 filed Sep. 13, 2017.

U.S. Appl. No. 15/805,025 filed Nov. 6, 2017 U.S. Pat. No. 20180133486 A1.

\* cited by examiner

COCHLEAR IMPLANTS HAVING MRI-COMPATIBLE MAGNET APPARATUS AND ASSOCIATED METHODS

CROSS-REFERENCE TO RELATED APPLICATIONS

This application is the U.S. National Stage of PCT App. Ser. No. PCT/US2016/033944, filed May 24, 2016, which is a continuation-in-part of, and claims priority to, International Application No. PCT/US2015/033040, filed May 28, 2015, which is incorporated herein by reference in its entirety.

BACKGROUND

1. Field

The present disclosure relates generally to the implantable portion of implantable cochlear stimulation (or "ICS") systems.

2. Description of the Related Art

ICS systems are used to help the profoundly deaf perceive a sensation of sound by directly exciting the intact auditory nerve with controlled impulses of electrical current. Ambient sound pressure waves are picked up by an externally worn microphone and converted to electrical signals. The electrical signals, in turn, are processed by a sound processor, converted to a pulse sequence having varying pulse widths and/or amplitudes, and transmitted to an implanted receiver circuit of the ICS system. The implanted receiver circuit is connected to an implantable electrode array that has been inserted into the cochlea of the inner ear, and electrical stimulation current is applied to varying electrode combinations to create a perception of sound. The electrode array may, alternatively, be directly inserted into the cochlear nerve without residing in the cochlea. A representative ICS system is disclosed in U.S. Pat. No. 5,824,022, which is entitled "Cochlear Stimulation System Employing Behind-The-Ear Sound processor With Remote Control" and incorporated herein by reference in its entirety. Examples of commercially available ICS sound processors include, but are not limited to, the Advanced Bionics™ Harmony™ BTE sound processor, the Advanced Bionics™ Naida™ BTE sound processor and the Advanced Bionics™ Neptune™ body worn sound processor.

As alluded to above, some ICS systems include an implantable cochlear stimulator (or "cochlear implant"), a sound processor unit (e.g., a body worn processor or behind-the-ear processor), and a microphone that is part of, or is in communication with, the sound processor unit. The cochlear implant communicates with the sound processor unit and, some ICS systems include a headpiece that is in communication with both the sound processor unit and the cochlear implant. The headpiece communicates with the cochlear implant by way of a transmitter (e.g., an antenna) on the headpiece and a receiver (e.g., an antenna) on the implant. Optimum communication is achieved when the transmitter and the receiver are aligned with one another. To that end, the headpiece and the cochlear implant may include respective positioning magnets that are attracted to one another, and that maintain the position of the headpiece transmitter over the implant receiver. The implant magnet may, for example, be located within a pocket in the cochlear implant housing.

The present inventors have determined that conventional cochlear implants are susceptible to improvement. For example, the magnets in many conventional cochlear implants are disk-shaped and have north and south magnetic dipoles that are aligned in the axial direction of the disk. Such magnets are not compatible with magnetic resonance imaging ("MRI") systems. In particular, the cochlear implant 10 illustrated in FIG. 1 includes, among other things, a housing 12 and a disk-shaped solid block magnet 14. The implant magnet produces a magnetic field M in a direction that is perpendicular to the patient's skin and parallel to the Z-axis of the implant magnet, and this magnetic field direction is not aligned with, and may be perpendicular to (as shown), the direction of the MRI magnetic field B. The misalignment of the interacting magnetic fields M and B is problematic for a number of reasons. The dominant MRI magnetic field B (typically 1.5 Tesla or more) may demagnetize the implant magnet 14 or generate a significant amount of torque T on the implant magnet 14. The torque T may dislodge the implant magnet 14 from the pocket within the housing 12, reverse the magnet 14 and/or dislocate the cochlear implant 10, all of which may also induce tissue damage. One proposed solution involves surgically removing the implant magnet 14 prior to the MRI procedure and then surgically replacing the implant magnet thereafter. The present inventors have determined that a solution which does not involve surgery would be desirable.

SUMMARY

A cochlear implant in accordance with one of the present inventions includes a cochlear lead, an antenna, a stimulation processor, a magnet apparatus, associated with the antenna, including a case with an internal volume, a divider that separates the internal volume into a plurality of sub-volumes, and respective pluralities of magnetic material particles packed within the sub-volumes in such a manner that adjacent magnetic material particles are in contact with one another and are also movable relative to one another. The present inventions also include systems with such a cochlear implant in combination with a sound processor.

There are a number of advantages associated with such implants and systems. For example, a strong magnetic field, such as an MRI magnetic field, will not demagnetize the magnet apparatus. Nor will it generate a significant amount of torque on the magnet apparatus and associated cochlear implant. As a result, surgical removal of the cochlear implant magnet prior to an MRI procedure, and then surgically replacement thereafter, is not required.

A cochlear implant in accordance with one of the present inventions includes a cochlear lead, a flexible housing defining an exterior, a magnet pocket and an elongate slot that extends from the exterior to the magnet pocket, an antenna within the flexible housing, and a stimulation processor, operably connected to the antenna and to the cochlear lead, within the flexible housing. The present inventions also include systems with such a cochlear implant in combination with a sound processor.

There are a number of advantages associated with such implants and systems. For example, the magnet retainer defined by the portion of the housing over the magnet pocket will be stronger than the magnet retainer associated with a circular magnet opening. The smaller open area defined by the elongate slot also reduces the likelihood of biofilm formation, as compared to larger circular openings.

A cochlear implant in accordance with one of the present inventions includes a cochlear lead, a flexible housing defining a square magnet pocket, a square antenna within the flexible housing that extends around the square magnet pocket, and a stimulation processor.

There are a number of advantages associated with such implants and systems. For example, a square magnet apparatus contains more magnetic material than a circular magnet with a diameter that is equal to the length and width of the square magnet apparatus. The corners of the square magnet apparatus also facilitate insertion of the magnet apparatus through an elongate slot.

The above described and many other features of the present inventions will become apparent as the inventions become better understood by reference to the following detailed description when considered in conjunction with the accompanying drawings.

BRIEF DESCRIPTION OF THE DRAWINGS

Detailed descriptions of the exemplary embodiments will be made with reference to the accompanying drawings.

DETAILED DESCRIPTION OF THE EXEMPLARY EMBODIMENTS

The following is a detailed description of the best presently known modes of carrying out the inventions. This description is not to be taken in a limiting sense, but is made merely for the purpose of illustrating the general principles of the inventions.

Figure 2A:
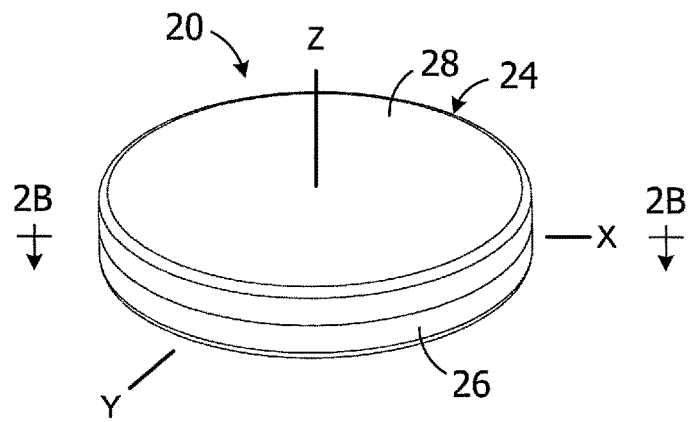
FIG. 2A is a perspective view of an implant magnet apparatus in accordance with one embodiment of a present invention.
Figure 2B:
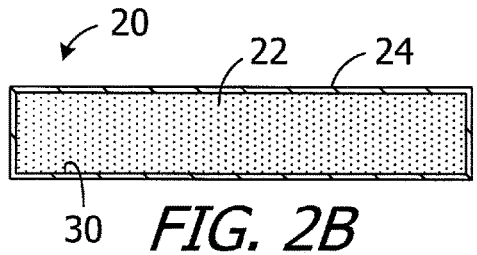
FIG. 2B is a section view taken along line 2B-2B in FIG. 2A.

As illustrated for example in FIGS. 2A and 2B, an exemplary implant magnet apparatus (or "magnet apparatus") 20 includes magnetic material particles (or "particles") 22 within the internal volume of a case 24. The particles 22, which are discussed in greater detail below with reference to FIGS. 4A-6B, are in contact with one another and are independently and freely rotatable and otherwise movable relative to one another and to the case. The particles 22 are free to move from one X-Y-Z coordinate to another and/or rotate in any direction. For example, some particles 22 may move linearly and/or rotate relative to other particles and relative to the case 24, while the orientation of the case remains the same, when the magnet apparatus 20 is exposed to an external magnetic field. The magnet apparatus 20, as well as the other magnet apparatus described herein, may be incorporated into a cochlear implant in the manner described in greater detail below.

The case 24 is not limited to any particular configuration, size or shape. In the illustrated implementation, the case 24 includes a base 26 and a cover 28 that may be secured to base after the magnetic material particles 22 have been dispensed into the base. The cover 28 may be secured to the base 26 in such a manner that a hermetic seal is formed between the cover and the base. Suitable techniques for securing the cover 28 to the base 26 include, for example, seam welding with a laser welder. With respect to materials, the case 24 may be formed from biocompatible paramagnetic metals, such as titanium or titanium alloys, and/or biocompatible non-magnetic plastics such as polyether ether ketone (PEEK), low-density polyethylene (LDPE), high-density polyethylene (HDPE) and polyamide. In particular, exemplary metals include commercially pure titanium (e.g., Grade 2) and the titanium alloy Ti-6Al-4V (Grade 5), while exemplary metal thicknesses may range from 0.20 mm to 0.25 mm. With respect to size and shape, the case 24 may have an overall size and shape similar to that of conventional cochlear implant magnets so that the magnet apparatus 20 can be substituted for a conventional magnet in an otherwise conventional cochlear implant. The exemplary case 24 is disk-shaped and defines an X-axis, a Y-axis and a Z-axis. In some implementations, the diameter that may range from 9 mm to 16 mm and the thickness may range from 1.5 mm to 3.0 mm. The diameter of the case 24 is 12.9 mm, and the thickness is 2.4 mm, in the illustrated embodiment.

Figure 2C:
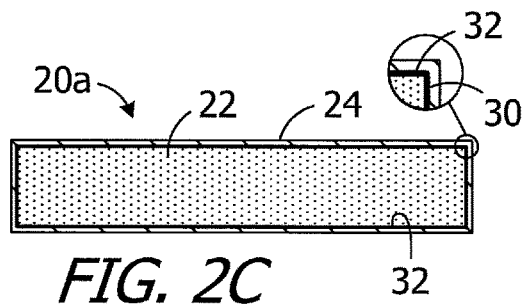
FIG. 2C is a section view of an implant magnet apparatus in accordance with one embodiment of a present invention.

The magnet apparatus 20 includes an inner surface 30 which, in this embodiment, is formed by the inner surface of the case 24, i.e., the inner surfaces of the base 26 and cover 28. A lubricious layer may be added to the inner surface to improve the movement of the particles 22 that are adjacent to the inner surface 30. To that end, and referring to the magnet apparatus 20a illustrated in FIG. 2C, which is otherwise identical to the magnet apparatus 20, a lubricious layer 32 covers the inner surface 30 of the case 24. The lubricious layer 32 may be in the form of a specific finish of the inner surface that reduces friction, as compared to an unfinished surface, or may be a coating of a lubricious material such as polytetrafluoroethylene (PTFE), Parylene, or fluorinated ethylene propylene (FEP). In those instances where the base 26 is formed by stamping, the finishing process may occur prior to stamping.

Figure 3A:
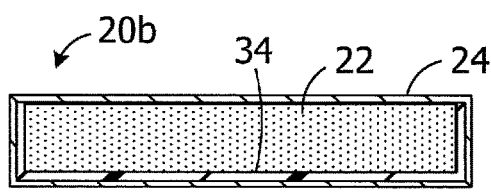
FIG. 3A is a section view of an implant magnet apparatus in accordance with one embodiment of a present invention.

The exemplary magnet apparatus 20b illustrated in FIG. 3A is substantially similar to magnet apparatus 20 and similar elements are represented by similar reference numerals. Here, however, a shim 34 may be inserted into the case 24 to focus the magnetic field created by the magnetic material particles 22. More specifically, when the associated cochlear implant is implanted, the shim 34 (sometimes referred to as a "flux guide") will increase the flux density and focus the magnetic field toward the patient's skin and an externally worn headpiece. Although the present shims are not so limited, the exemplary shim 34 is cup-shaped and may be about 0.25 mm thick and formed from iron or from a nickel-iron alloy, referred to as mu-metal, that is composed of approximately 77% nickel, 16% iron, 5% copper and 2% chromium or molybdenum. In other implementations, a flat disk positioned at the bottom of the base 26 may be employed.

Figure 3B:
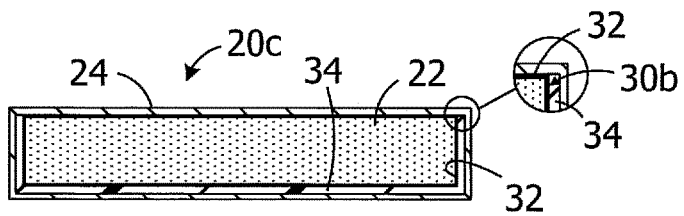
FIG. 3B is a section view of an implant magnet apparatus in accordance with one embodiment of a present invention.

Referring to FIG. 3B, the exemplary magnet apparatus 20c is substantially similar to magnet apparatus 20b in FIG. 3A and similar elements are represented by similar reference numerals. Here, however, a lubricious layer 32 covers the inner surface 30b of the magnet apparatus 20c. The inner surface 30b is formed by the inner surfaces of the cover 28 and the shim 34. The lubricious layer 32 may be formed in the manner discussed above with reference to FIG. 2C. In those instances where the shim 34 is formed by stamping, the finishing process may occur prior to stamping.

Figure 4A:
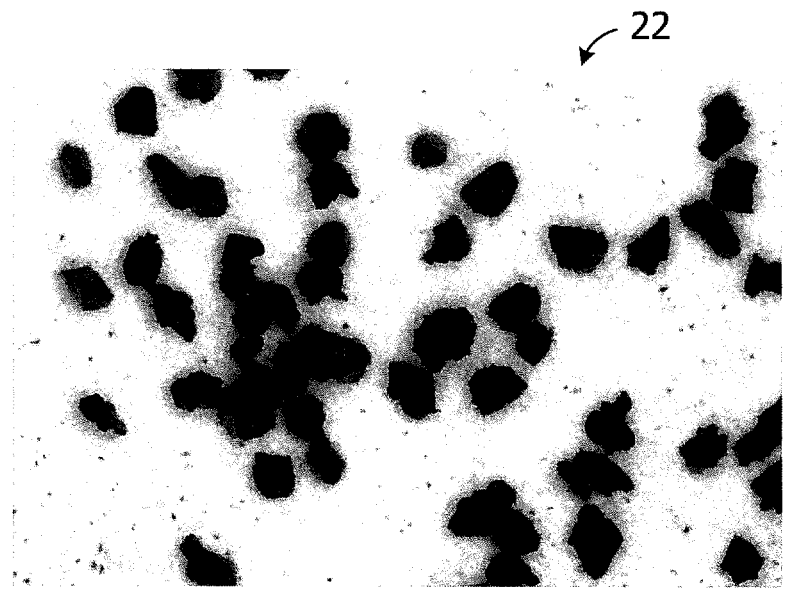
FIG. 4A is a magnified view of exemplary magnetic material particles.
Figure 4B:
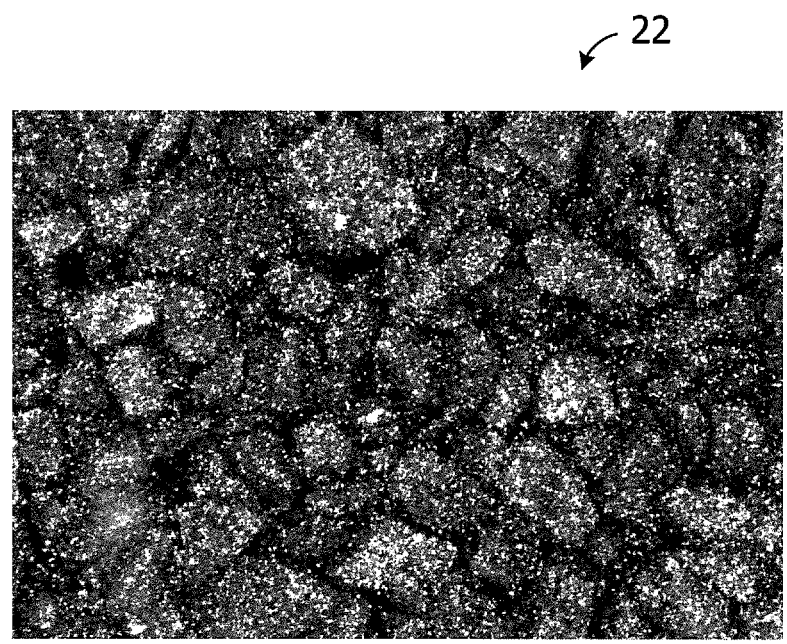
FIG. 4B is a magnified view of exemplary magnetic material particles in a loosely packed state
Figure 5A:
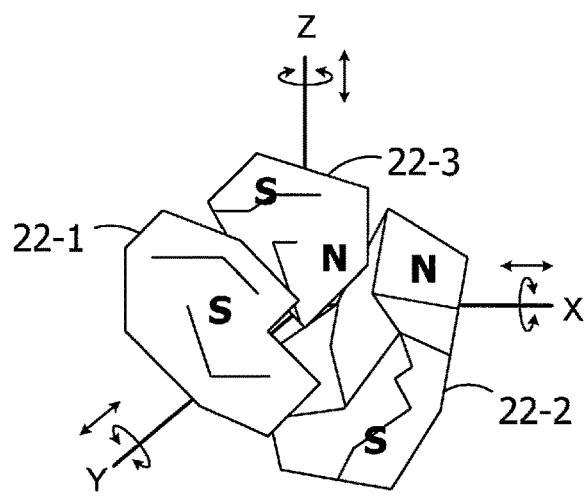
FIG. 5A is a perspective view of a plurality of magnetic material particles a loosely packed state prior to being exposed to a magnetic field.
Figure 5B:
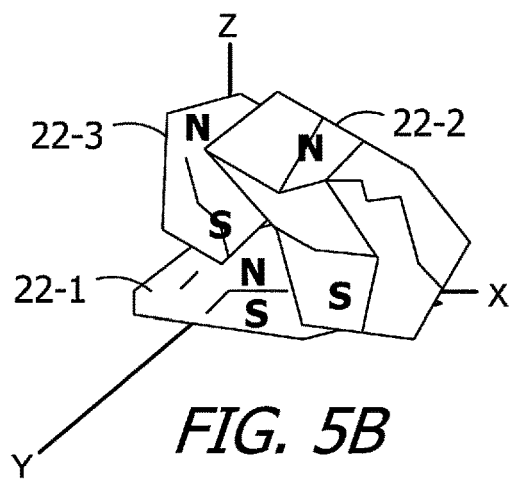
FIG. 5B is a perspective view of a plurality of magnetic material particles a loosely packed state after being exposed to a magnetic field.

Turning to FIGS. 4A and 4B, and although the present magnetic material particles are not limited to any particular shape unless so specified in a particular claim, the exemplary magnetic material particles 22 are non-spherical, polyhedral shapes or at least substantially polyhedral shapes, i.e., multi-sided shapes that are regular or irregular, symmetric or asymmetric, with or without smooth side surfaces, and with or without straight edges, that will permit the particles to rotate relative to one another when loosely packed. Any three-dimensional shapes that permit the movement described herein may also be employed. The magnetic material particles 22 may be formed from any suitable magnetic material. Such materials include, but are not limited to, neodymium-iron-boron ("$Nd_2Fe_{14}B$") magnetic material, isotropic neodymium, anisotropic neodymium, samarium-cobalt ("$Sm_2Co_{17}$"). The at least substantially polyhedral shapes illustrated in FIGS. 4A and 4B are the fractured pieces of a larger magnet that are created by a magnet crushing process. The present particles may have a mesh size that ranges from 50 μm to 500 μm, or from 100 μm to 300 μm, or from 300 μm to 500 μm, and the shape and size may vary from particle to particle. The particles 22, which are not suspended in liquid or any other carrier, may be packed loosely and pressed with a slight force of, for example, 100 kPa (0.14 psi) in order to insure that adjacent particles will be in contact with one another (FIG. 4B), yet will also be independently movable and movable relative to one another. To that end, and referring to FIGS. 5A and 5B, three exemplary particles 22-1, 22-2 and 22-3 are shown in both arbitrary orientations prior to being exposed to a magnetic field (FIG. 5A) and after they have been aligned with a magnetic field (FIG. 5B). The reorientation-related movement of the particles 22-1, 22-2 and 22-3, which varies from one particle to another, may entail rotation about, and/or movement in the direction of, the X-axis, the Y-axis, and/or the Z-axis, and any and all combinations thereof.

The magnetic material density ratio within the case 24, i.e. the ratio of the total volume of magnetic material particles to the total volume within the case 24, may be at least 70%, i.e., there is no more than 30% free space within the case. This ratio allows the present magnet apparatuses 20-20h (magnet apparatuses 20c-20h are described below) to be essentially the same size and shape as a conventional disk-shaped permanent magnet in a cochlear implant when combined with an appropriate headpiece. With respect to the density of the magnetic material particles, the density may range, in the exemplary context of neodymium-iron-boron, from 2.75 g/cm$^3$ (30% free space) to 3.94 g/cm$^3$ (fully packed and pressed with a force of 100 kPa). Free space percentages that are larger than 30% may be employed in those instances where the magnet apparatus is larger. The magnetic strength of the of the exemplary magnet apparatus 20b, which includes the particles 22 within the case 24 and a shim 34, is about 60-70 gauss measured at a distance of 1 mm from the case on the Z-axis. The pull force between a cochlear implant including the magnet apparatus 20 and a cochlear implant headpiece (e.g., headpiece 300 in FIG. 39), including headpieces that have one or more magnets therein, at a distance of 3 mm may be about 2.2±0.1 N. The 3 mm distance corresponds to the distance (or "air gap") between the implant magnet apparatus and the headpiece magnet (or magnet apparatus) during pull force testing, and the pull force will be different at other testing distances. Various headpiece magnet apparatus configurations which, when combined with an implant magnet apparatus in a system that includes both a cochlear implant and a cochlear implant headpiece, and where the pull force between the headpiece magnet apparatus and the implant magnet apparatus is about 2.2±0.1 N, are discussed below with reference to FIG. 40.

It should also be noted that the use of significantly larger magnetic elements within the case in place of the magnetic material particles will decrease the magnetic material density (due to air gaps between the magnetic elements) and prevent magnet apparatus which have cases of the sizes and shapes disclosed herein from achieving the desired level of magnetic strength. Similarly, the use of ferrofluids, which include nano-sized particles dispersed and suspended within a fluid, in place of the magnetic material particles would also necessitate the use of a case that is larger than a conventional cochlear implant magnet to achieve the desired level of magnetic strength.

Figure 6A:
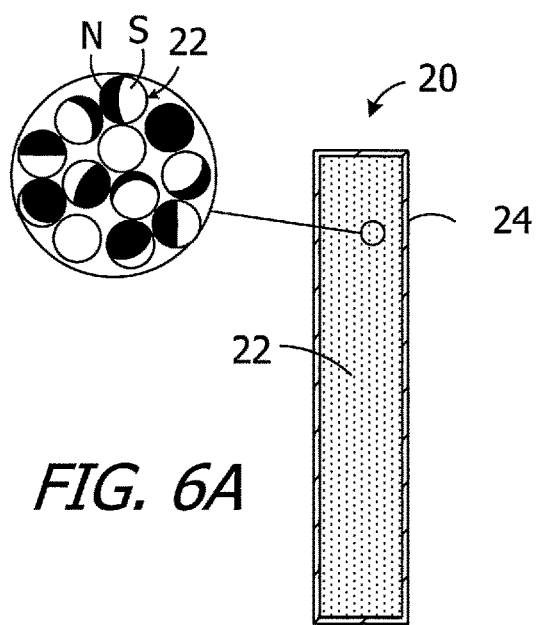
FIG. 6A is a section view of the implant magnet apparatus illustrated in FIG. 2 prior to being exposed to a magnetic field.
Figure 6B:
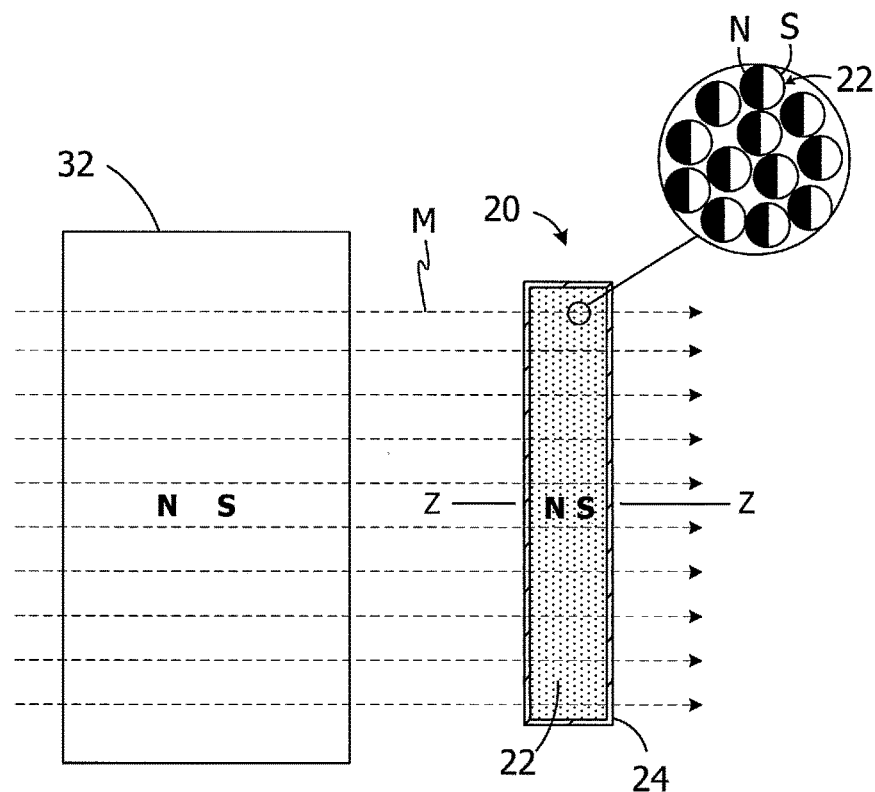
FIG. 6B is a section view of the implant magnet apparatus illustrated in FIG. 2 being exposed to a magnetic field.

For ease of illustration purposes on only, the non-spherical particles may be represented in the manner shown in FIGS. 6A and 6B. The north pole N of each particle 22 is black (or grey) and the south pole S is white. The respective N-S orientations of the particles 22 will vary from one particle to the next, with the particles being magnetically attracted to one other in arbitrary directions, after the particles have been dispensed into the case 24. The particles 22 will remain in their random angular orientations until they are reoriented by a magnetic field in the manner described below. Such reorientation is possible because the particles 22 are independently movable relative to one another in any and all directions. Relative movement of the particles 22 may entail rotation about the X-axis, or rotation about the Y-axis, or rotation about the Z-axis, and/or any and all combinations thereof, and/or non-rotational movement in the X-direction, or the Y-direction, or the Z-direction, and/or any and all combinations thereof.

An external magnetic field may be used to reorient the magnetic material particles 22 within the case 24 to establish the desired N-S orientation of magnet apparatuses 20-20h. Such reorientation may be performed before or after the magnet apparatuses 20-20h are incorporated into a cochlear implant. To that end, and referring to FIG. 6B, the magnet apparatus may be exposed to the magnetic field M of the magnet 32. With the exception of those particles 22 that were by chance already aligned with the magnetic field M, the particles 22 will rotate into alignment with the magnetic field M (e.g., from the orientation illustrated in FIG. 6A to the orientation illustrated in FIG. 6B), thereby establishing the intended N-S orientation of the magnet apparatus 20. Here, the intended N-S orientation is parallel to the Z-axis of the disk-shaped magnet apparatus 20.

Figure 7:
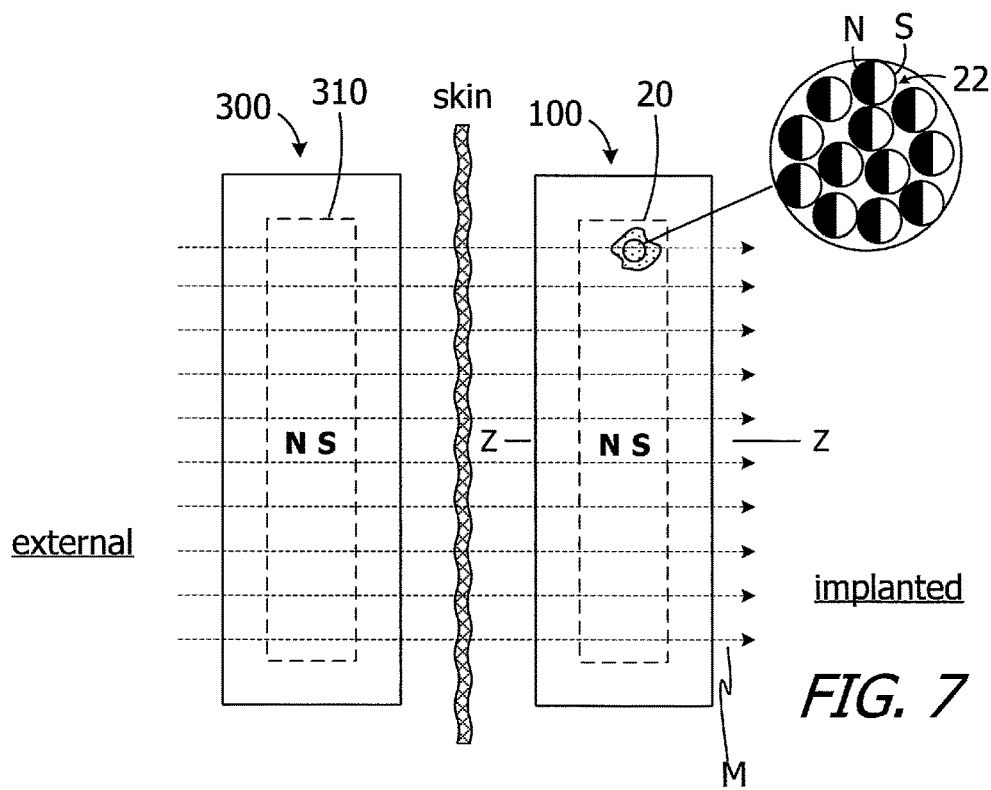
FIG. 7 is a plan, cutaway view showing a cochlear implant in accordance with one embodiment of a present invention being used in conjunction with a cochlear implant headpiece.

The magnet apparatus 20 (or 20a-20c above or 20d-20h below) may form part of a cochlear implant in a cochlear implant system that also includes a sound processor and a headpiece. One example of such a cochlear implant system is the system 50, which is described in greater detail below with reference to FIG. 39, and which includes a cochlear implant 100 and a headpiece 300. As illustrated for example in FIG. 7, the implant 100 includes the magnet apparatus 20. The N-S orientation of the magnet apparatus 20 is the same as the orientation illustrated in FIG. 6. The headpiece 300, which includes a magnet apparatus 310 with the same N-S orientation, may be held in place by virtue of the attraction between the magnet apparatus 20 and the magnet apparatus 310. The Z-axis of the magnet apparatus 20 is perpendicular to the patient's skin and parallel to the magnetic field M. Communication between the headpiece 300 and cochlear implant 100 may then occur in conventional fashion.

Figure 1:
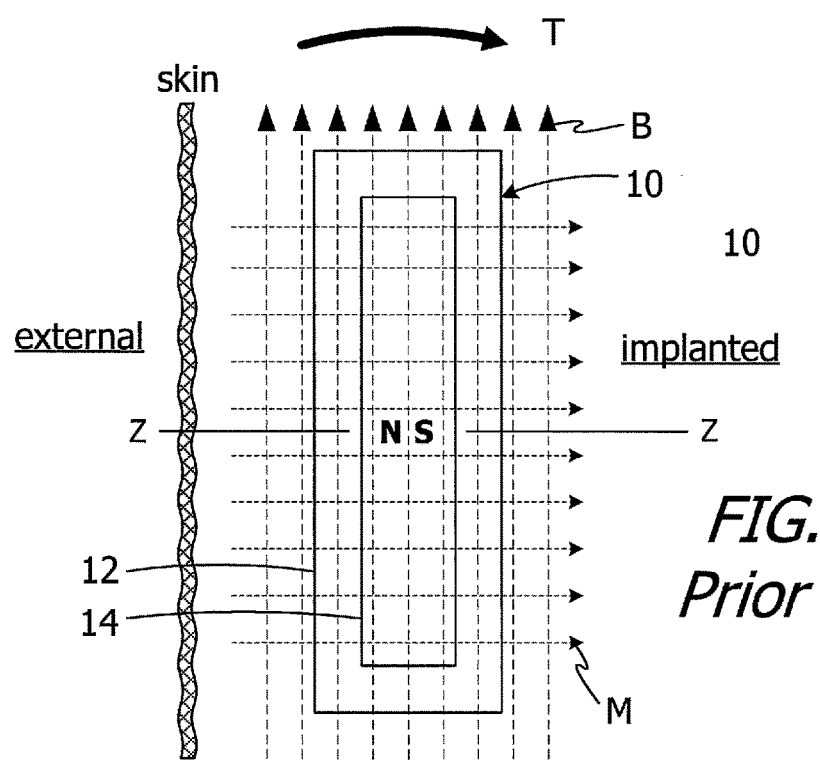
FIG. 1 is a plan view showing a conventional cochlear implant in an MRI magnetic field.
Figure 8:
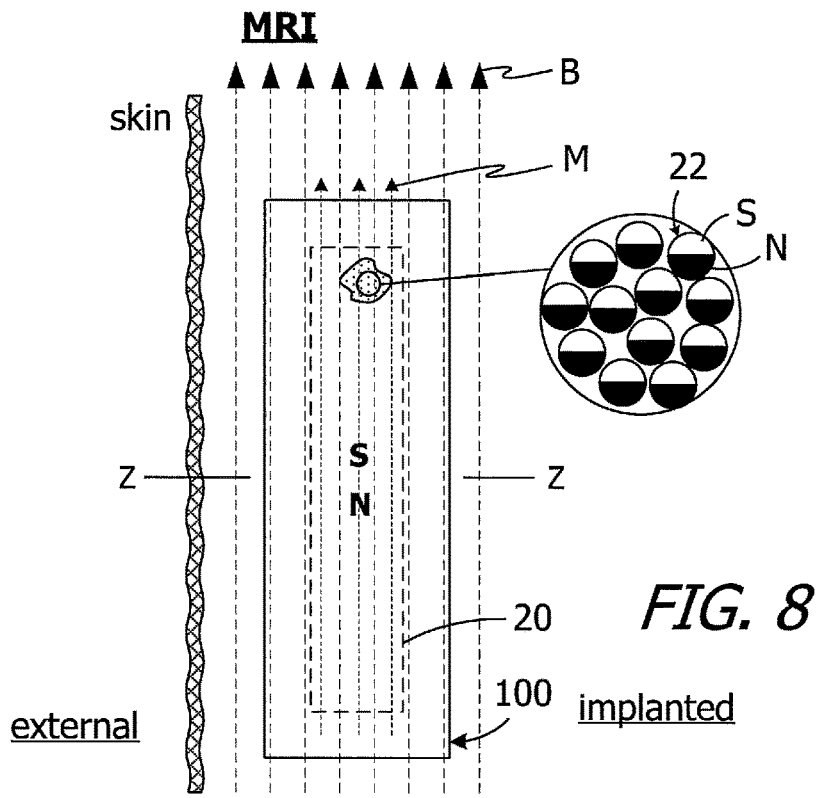
FIG. 8 is a plan, cutaway view showing a cochlear implant in accordance with one embodiment of a present invention being exposed to an MRI magnetic field.

FIG. 8 shows the implanted cochlear implant 100 being exposed to an MRI magnetic field B. The orientation of the cochlear implant 100 is such that the Z-axis of the magnet apparatus 20 is perpendicular to the MRI magnetic field B. In contrast to the conventional magnet 14 illustrated in FIG. 1, however, the magnetic field M of the magnet apparatus 20 is not perpendicular to the MRI magnetic field B. Instead, the dominant MRI magnetic field B reorients magnetic material particles 22 relative to the case 24 and to the associated cochlear implant, from the orientation illustrated in FIG. 7 to the orientation illustrated in FIG. 8, such that the N-S orientation of the magnet apparatus 20 is perpendicular to the Z-axis and the magnetic field M is parallel to the MRI magnetic field B.

There are a variety of advantages associated with such magnetic field reorientation. For example, the MRI magnetic field B (typically 1.5 Tesla or more) will not demagnetize the magnet apparatus 20 or generate a significant amount of torque T on the magnet apparatus and associated cochlear implant. As a result, surgical removal of the cochlear implant magnet prior to an MRI procedure, and then surgically replacement thereafter, is not required.

Figure 9:
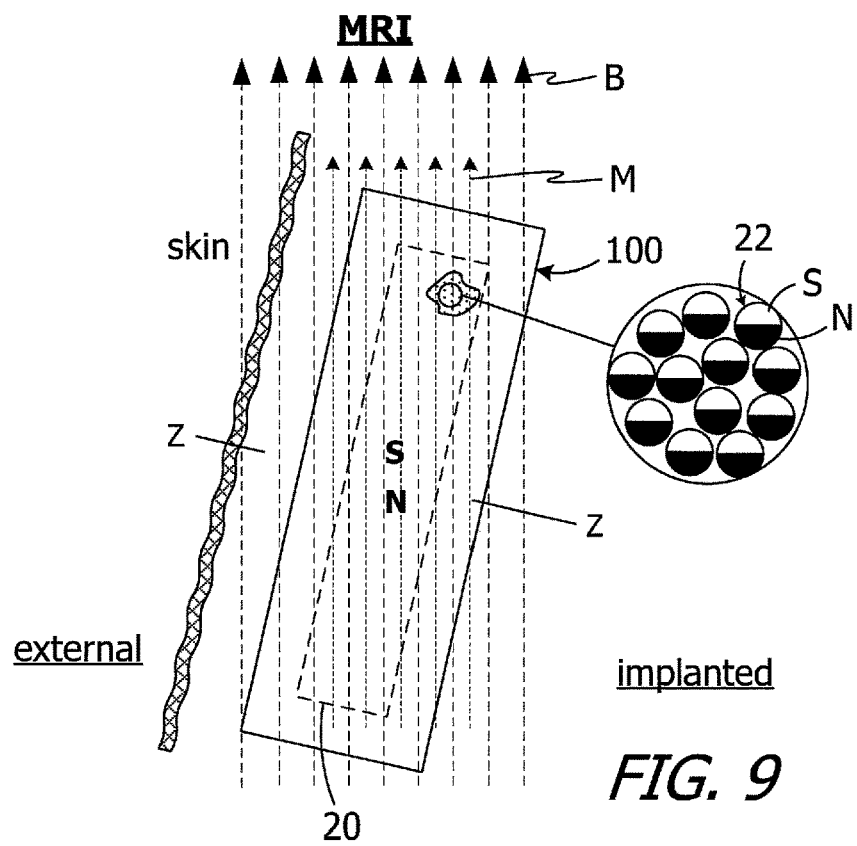
FIG. 9 is a plan, cutaway view showing a cochlear implant in accordance with one embodiment of a present invention being exposed to an MRI magnetic field.

It should also be noted that movement of the patient relative to the MRI magnetic field B while in the MRI magnetic field B will also result in reorientation of the magnetic material particles 22 within the case 24, as is illustrated in FIG. 9. Here, the N-S orientation of the magnet apparatus 20 neither perpendicular, nor parallel, to the Z-axis and the magnetic field M remains parallel to the MRI magnetic field B. The ability of the particles 22 to rotate and move relative to the case 24 about and along the X, Y and Z-axes, as well as any and all combinations of such rotation and movement (i.e., in any direction, and any rotational direction, relative to the case and relative to the remainder of the associated cochlear implant), allows the N-S orientation of the each particle 22 (and the magnet apparatus 20) to align itself with an MRI magnetic field B regardless of the relative orientations of the MRI magnetic field and the magnet apparatus. As the orientation of one or both of the MRI magnetic field B and the magnet apparatus 20 changes, the N-S orientation of the magnet apparatus 20 relative to the case 24 and Z-axis will change so as to maintain the alignment of the N-S orientation of the magnetic material particles 22 (as well as the magnet apparatus itself) with the MRI magnetic field.

After the MRI procedure has been completed, the implanted magnet apparatus may be exposed to a magnetic field (e.g., with the magnet 32) to return the particles 22 to their intended N-S orientation.

Magnet apparatus with magnetic material particles, such as the magnet apparatuses 20-20c described above, may also include a divider that separates the internal volume within the case into a plurality of sub-volumes. The divider limits particle migration and maintains an even distribution of the magnetic material particles. The even distribution results in proper alignment of the magnet apparatus with the associated headpiece magnet or magnet apparatus, which in turn results in proper alignment of the implant antenna with the headpiece antenna.

Figure 10:
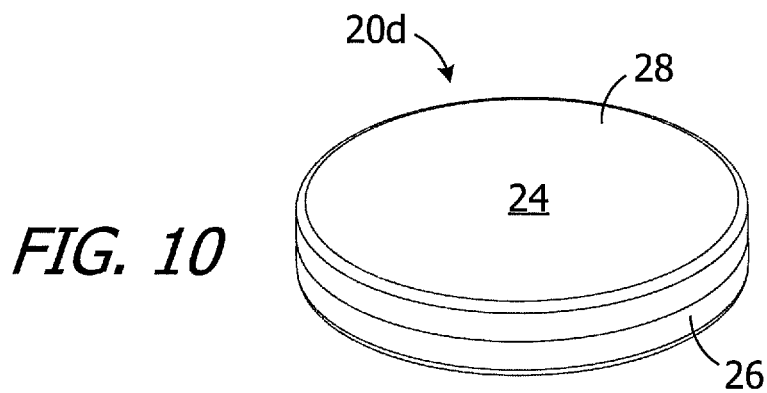
FIG. 10 is a perspective view of an implant magnet apparatus in accordance with one embodiment of a present invention.
Figure 11:
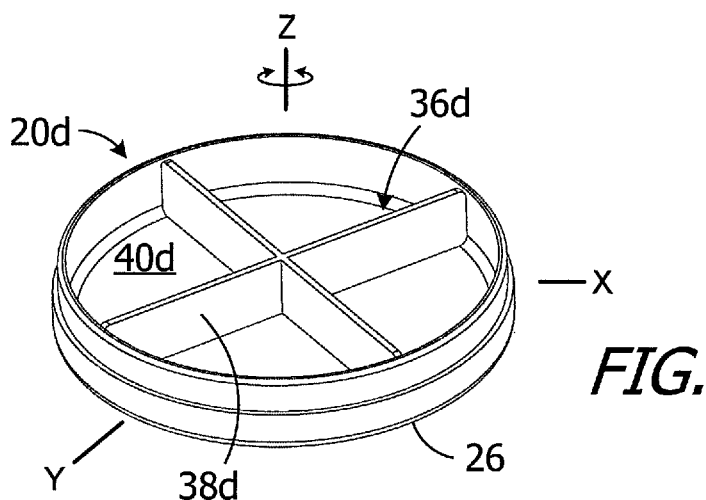
FIG. 11 is a perspective view of the implant magnet apparatus illustrated in FIG. 10 with the cover and magnetic material particles removed.
Figure 12:
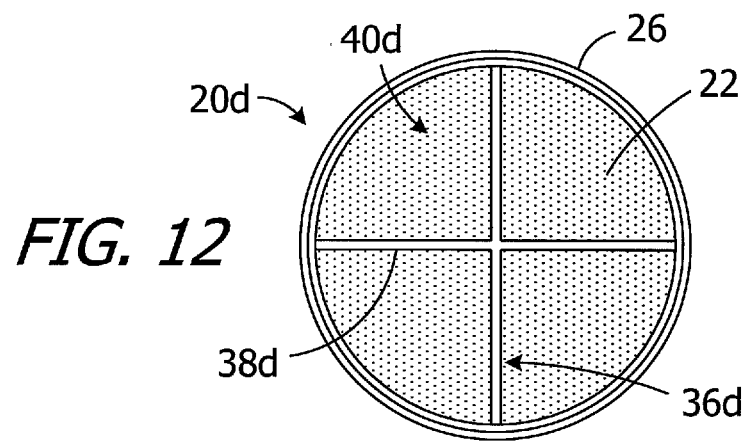
FIG. 12 is a plan view of the implant magnet apparatus illustrated in FIG. 10 with the cover removed.
Figure 13:
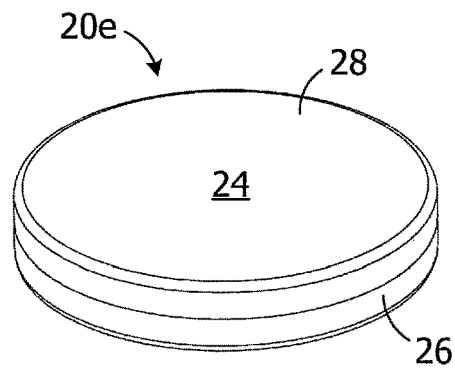
FIG. 13 is a perspective view of an implant magnet apparatus in accordance with one embodiment of a present invention.
Figure 14:
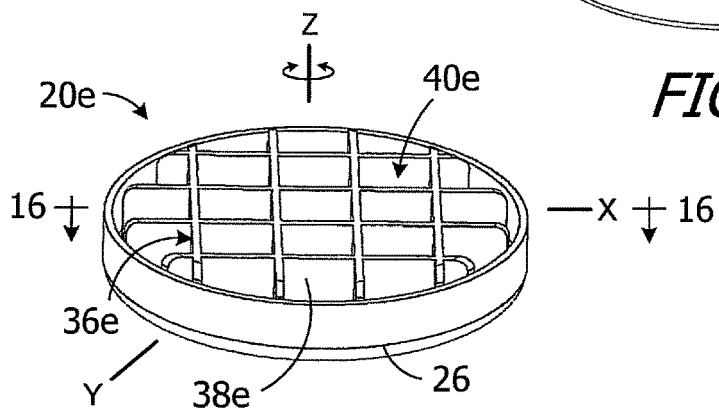
FIG. 14 is a perspective view of the implant magnet apparatus illustrated in FIG. 13 with the cover and magnetic material particles removed.
Figure 15:
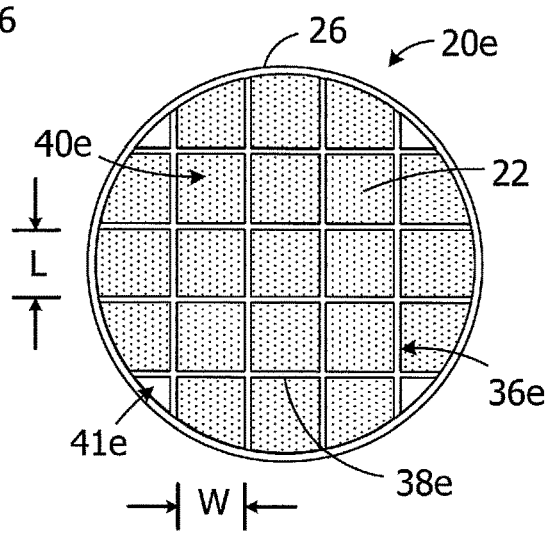
FIG. 15 is a plan view of the implant magnet apparatus illustrated in FIG. 13 with the cover removed.
Figure 16:
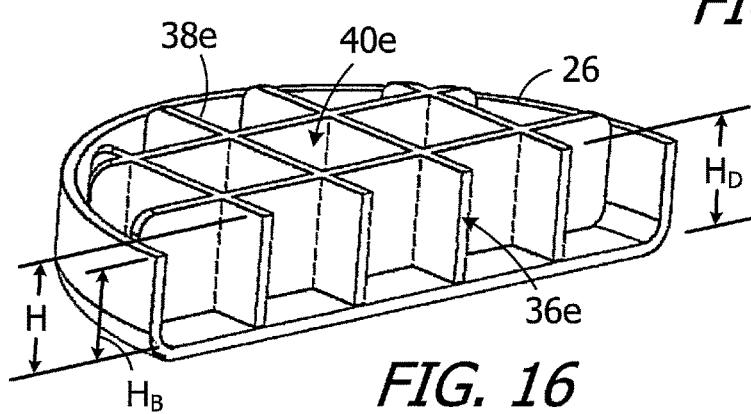
FIG. 16 is a perspective section view taken along line 16-16 in FIG. 14.

The exemplary magnet apparatus 20d illustrated in FIGS. 10-12 is substantially similar to magnet apparatus 20 in FIG. 2A and similar elements are represented by similar reference numerals. Here, however, a divider 36d is located within the internal volume of case 24. The divider 36d, which may include one or more walls 38d that extend from the internal volume to the top, separates the internal volume into a plurality of sub-volumes 40d and facilitates an even distribution of the magnetic material particles 22 within case 24. Although the exemplary divider 36d is X-shaped and includes four walls that divide the volume into four sub-volumes 40, any suitable divider configuration and number of sub-volumes may be employed, as is described below. Other exemplary divider configurations include, but are not limited to, an asterisk shape, a square grid, and a honeycomb. The position of the divider 36d may be fixed relative to the case 24 (as shown) by, for example, securing the divider to the base 26 with adhesive or with one or more welds, or the divider 36d may be rotatable about Z-axis relative to the case.

Suitable materials for the divider 36d (as well as the other dividers described below) include but are not limited to, plastics such as PEEK and PTFE and metals such as iron, titanium and mu-metal. The divider 36d, as well as the other dividers described below, may also be used in magnet apparatus that include a lubricious layer (see, e.g., FIG. 2C), a magnetic shim (see, e.g., FIG. 3A), or a magnetic shim and a lubricious layer (see, e.g., FIG. 3B).

Turning to FIGS. 13-16, exemplary magnet apparatus 20e is substantially similar to magnet apparatus 20d and similar elements are represented by similar reference numerals. Here, however, the divider 36e includes walls 38e and divides the internal volume into twenty-one (21) sub-volumes 40e for magnetic material particles 22 as well as four remainder volumes 41e that typically will not include magnetic material particles. The position of the divider 36e may be fixed relative to the case 24 (as shown) by, for example, securing the divider to the base 26 with adhesive or with one or more welds, or the divider 36e may be rotatable about Z-axis relative to the case 24.

The sub-volumes 40e are configured to optimize the relationship between the amount of magnetic material that is located within a sub-volume and the ability of the magnetic material particles to rotate relative to one another when exposed to a magnetic field. In particular, the sub-volumes 40e are three-dimensionally uniform or are at least substantially three-dimensionally uniform. As used herein, and referring to FIGS. 15 and 16, a "three-dimensionally uniform" sub-volume is a sub-volume that is equal length L, width W, and height H. As used herein, an "at least substantially three-dimensionally uniform" sub-volume is a sub-volume where the smallest of the length L, width W, and height H is no less than 20% of the largest of the length L, width W, and height H. Given that a magnet apparatus employed in a cochlear implant is a relatively flat structure, with the height H of the internal volume (measured in the Z-direction) significantly less than the diameter of the internal volume (measured in the X and Y-directions), the height H is the limiting factor in the three-dimensionally uniform (or at least substantially three-dimensionally uniform) sub-volumes 40e. As a result, there are far more sub-volumes in the magnet apparatus 20e than, for example, the magnet apparatus 20d illustrated in FIGS. 10-12 that without three-dimensionally uniform (or at least substantially three-dimensionally uniform).

In the exemplary implementation illustrated in FIGS. 13-16, the nine sub-volumes 40e closest to the Z-axis are cube-shaped and three-dimensionally uniform, while the twelve (12) sub-volumes 40e adjacent to the outer perimeter of the internal volume are at least substantially three-dimensionally uniform. The height H of the sub-volumes 40e is equal to the height $H_D$ of the divider 36e which, in turn, is equal to the distance between the top and bottom inner surfaces of the case 24. Put another way, the divider 36e extends from the base 26 to the cover 28.

The use of three-dimensionally uniform (or at least substantially three-dimensionally uniform) sub-volumes 40e in relatively flat magnet apparatus 20e reduces large volume magnetic clumping by reducing the volume of magnetic material particles 22 within a given sub-volume, as compared to non-three-dimensionally uniform such as those shown in FIGS. 11 and 12. As a result, the torque produced by the magnetic material particles 22 exposed to a magnetic field is greatly reduced. The smaller sub-volumes 40e also make it easier to evenly distribute the magnetic material particles 22 during assembly of the magnet apparatus 20e. The smaller sub-volumes 40e also maintain a more even distribution of the magnetic material particles 22 with the internal volume.

It should also be noted that the height $H_B$ of the case base 26 (measured from the bottom inner surface) is less that the height $H_D$ of the divider 36e. The base height $H_B$ may be, for example, from 90% to 99% the divider height $H_D$, and is 90% in the illustrated implementation. During assembly of the magnet apparatus 20e, the magnetic material particles 22 may be packed tightly up to the top of the base 26 and pressed with a force of, for example, 100 kPa (0.14 psi) in order to insure that adjacent particles will be in tight contact with one another up to the top of the base 26. There will be no magnetic material particles 22 in the upper 10% of each sub-volume 40e. Some magnetic material particles 22 will, however, migrate into the upper 10% of each sub-volume 40e after the cover 28 has been secured to the base 26. The magnetic material density ratio within the case 24, i.e. the ratio of the total volume of magnetic material particles to the total volume within the case 24, will then be at least 70%, i.e., there is no more than 30% free space within the case.

Figure 17:
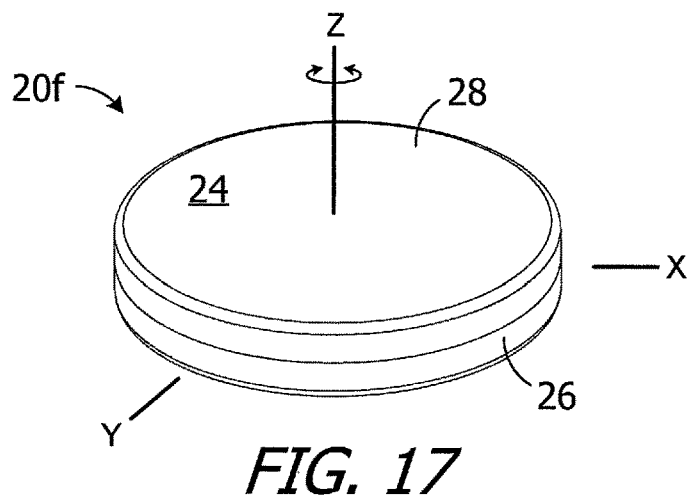
FIG. 17 is a perspective view of an implant magnet apparatus in accordance with one embodiment of a present invention.
Figure 18:
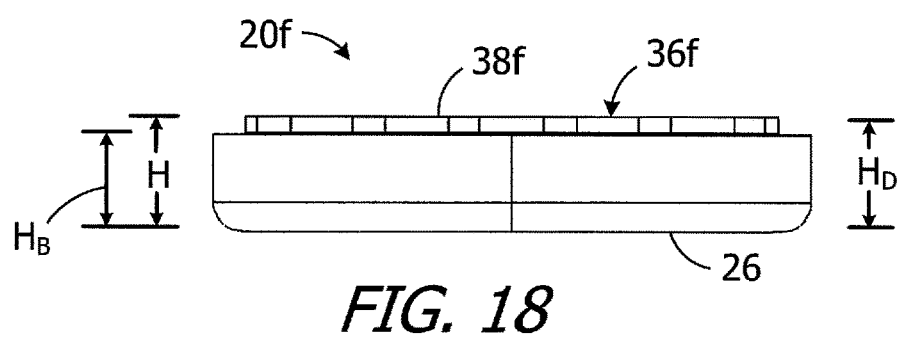
FIG. 18 is a side view of the implant magnet apparatus illustrated in FIG. 17 with the cover removed.
Figure 19:
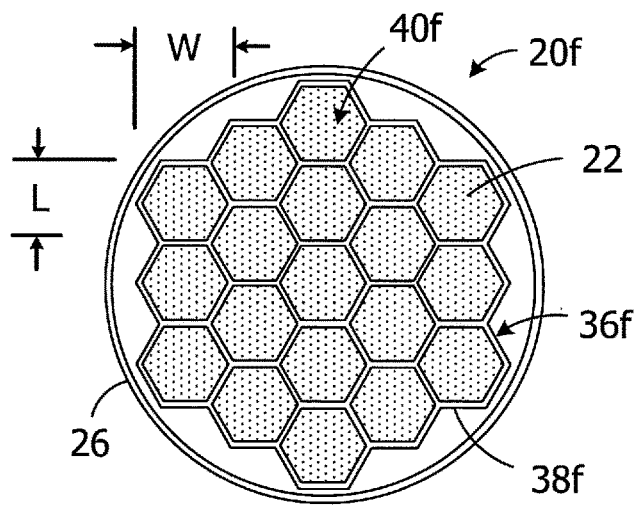
FIG. 19 is a plan view of the implant magnet apparatus illustrated in FIG. 17 with the cover removed.

Turning to FIGS. 17-19, the exemplary magnet apparatus 20f is substantially similar to magnet apparatus 20e and similar elements are represented by similar reference numerals. Here, however, the divider 36f includes walls 38f that divides the internal volume into nineteen sub-volumes 40f for magnetic material particles 22. The sub-volumes 40f are hexagonal shaped and, with respect to the relationship between length L, width W and height H of the sub-volumes, are at least substantially three-dimensionally uniform. The position of the divider 36f may be fixed relative to the case 24 (as shown) by, for example, securing the divider to the base 26 with adhesive or with one or more welds, or the divider 36f may be rotatable about Z-axis relative to the case. The height $H_B$ of the case base 26 is less that the height $H_D$ of the divider 36f. As noted above in the context of magnet apparatus 20e, the base height $H_B$ may be, for example, from 90% to 99% the divider height $H_D$, and is 90% in the illustrated implementation, and the divider height $H_D$ is equal to the height H of the sub-volumes 40f.

Figure 20:
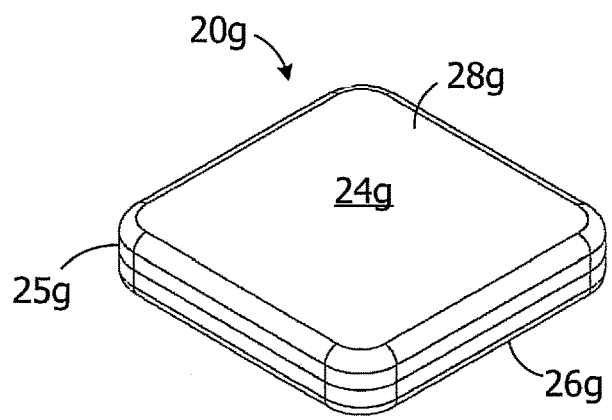
FIG. 20 is a perspective view of an implant magnet apparatus in accordance with one embodiment of a present invention.
Figure 21:
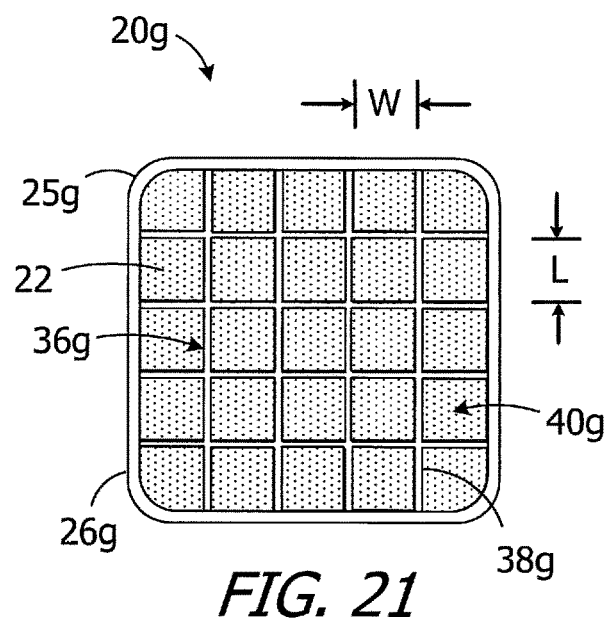
FIG. 21 is a plan view of the implant magnet apparatus illustrated in FIG. 20 with the cover removed.
Figure 22:
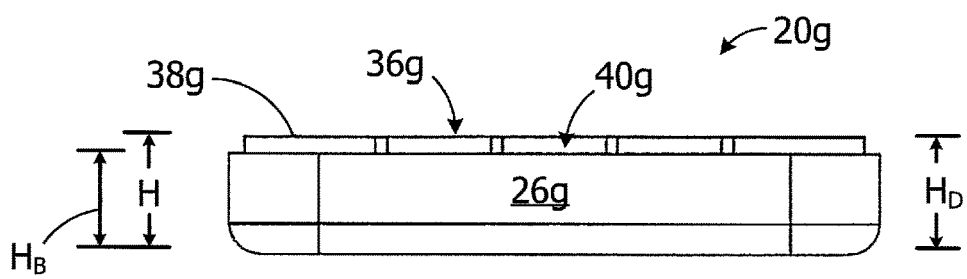
FIG. 22 is a side view of the implant magnet apparatus illustrated in FIG. 20 with the cover removed.

As illustrated for example in FIGS. 20-22, the exemplary magnet apparatus 20g is substantially similar to magnet apparatus 20e and similar elements are represented by similar reference numerals. Here, however, the case 24g (which includes a base 26g and a cover 28g) has a square shape that is defined by its two largest dimensions, i.e., the length and width. Such magnet apparatus are referred to below as "square magnet apparatus." The corners 25g are rounded in the illustrated embodiment, but may be sharp in other implementations. The divider 36g includes walls 38g that divide the internal volume into twenty-five (25) sub-volumes 40g for magnetic material particles 22. The sub-volumes 40f are cube-shaped and, with respect to the relationship between length L, width W and height H of the sub-volumes, are three-dimensionally uniform with the exception of the at least substantially three-dimensionally uniform sub-volumes at the rounded corners. The height $H_B$ of the case base 26g is less that the height $H_D$ of the divider 36g. As noted above in the context of magnet apparatus 20e, the base height $H_B$ may be, for example, from 90% to 99% the divider height $H_D$, and is 90% in the illustrated implementation, and the divider height $H_D$ is equal to the height H of the sub-volumes 40g.

There are a number of advantages associated with the use of square magnet apparatus. By way of example, a square magnet apparatus contains more magnetic material than a circular magnet with a diameter that is equal to the length and width of the square magnet apparatus. The square magnet apparatus also has more three-dimensionally uniform sub-volumes. Additionally, although the distance between the antenna and the corners of the square magnet apparatus is less than the distance between the antenna and the outer perimeter of a circular magnet apparatus with a diameter equal to the length and width of the square magnet apparatus, the effect of the square magnet apparatus on the efficiency of the antenna is less than that of the circular magnet apparatus. Only a small portion of the square magnet apparatus (i.e., the corners) is closer to the antenna than the entire perimeter of the circular magnet apparatus. The corners of the square magnet apparatus also facilitate insertion of the magnet apparatus through an elongate slot, as described below with reference to FIG. 35.

Figure 23:
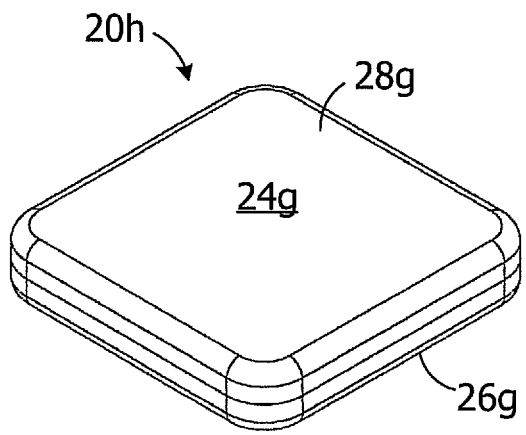
FIG. 23 is a perspective view of an implant magnet apparatus in accordance with one embodiment of a present invention.
Figure 24:
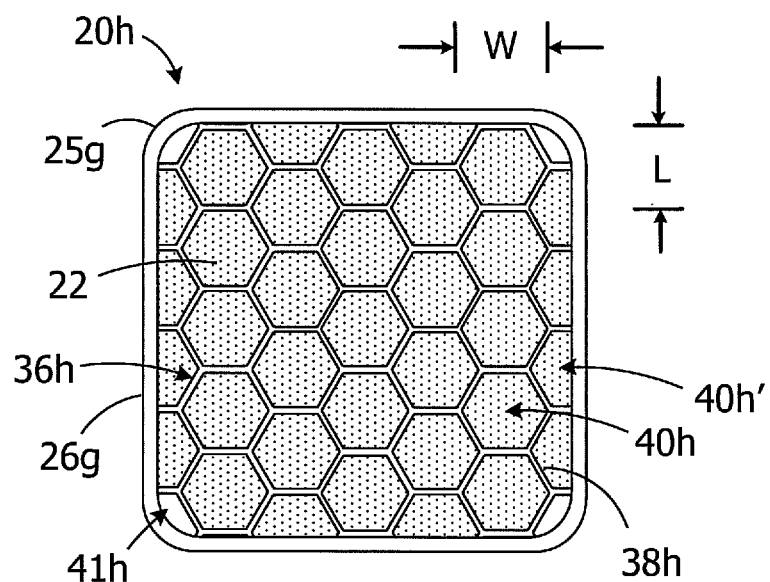
FIG. 24 is a plan view of the implant magnet apparatus illustrated in FIG. 23 with the cover removed.
Figure 25:
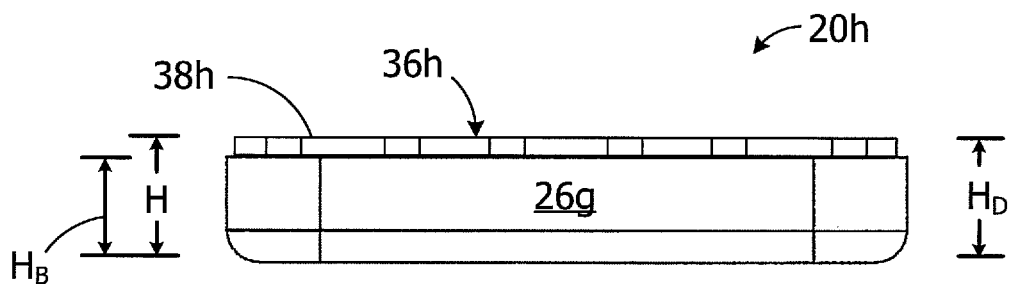
FIG. 25 is a side view of the implant magnet apparatus illustrated in FIG. 23 with the cover removed.

Turning to FIGS. 23 and 24, the exemplary magnet apparatus 20h is substantially similar to magnet apparatus 20g and similar elements are represented by similar reference numerals. Here, however, the divider 36h includes walls 38h that divide the internal volume of the case 24g into twenty three (23) hexagonal and, with respect to the relationship between length L, width W and height H of the sub-volumes, at least substantially three-dimensionally uniform sub-volumes 40h for magnetic material particles 22, twelve (12) partial hexagonal sub-volumes 40h' which may (as shown) or may not include magnetic material particles, and four remainder volumes 41h that typically will not include magnetic material particles. The height $H_B$ of the case base 26g is less that the height $H_D$ of the divider 36h. As noted above in the context of magnet apparatus 20e, the base height $H_B$ may be, for example, from 90% to 99% the divider height $H_D$, and is 90% in the illustrated implementation, and the divider height $H_D$ is equal to the height H of the sub-volumes 40h.

Figure 26:
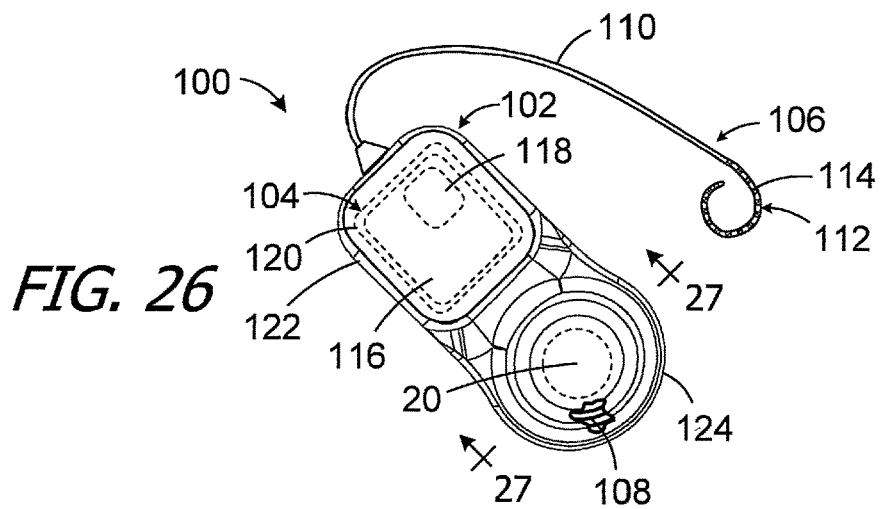
FIG. 26 is a plan view of a cochlear implant in accordance with one embodiment of a present invention.

One example of a cochlear implant (or "implantable cochlear stimulator") including the present magnet apparatus 20 (or one of magnet apparatus 20a-20f) is the cochlear implant 100 illustrated in FIG. 26. The exemplary cochlear implant 100 includes a resilient flexible housing 102 formed from a silicone elastomer or other suitable material, a processor assembly 104, a cochlear lead 106, and an antenna 108 that may be used to receive data and power by way of an external antenna that is associated with, for example, a sound processor unit. The cochlear lead 106 may include a flexible body 110, an electrode array 112 at one end of the flexible body 102, and a plurality of wires (not shown) that extend through the flexible body from the electrodes 114 (e.g., platinum electrodes) in the array 112 to the other end of the flexible body. The exemplary antenna 108 is a coil antenna with one or more loops (or "turns"), and three loops are shown in the illustrated embodiment. The exemplary processor assembly 104, which is connected to the electrode array 112 and antenna 108, includes a printed circuit board 116 with a stimulation processor 118 that is located within a hermetically sealed case 120. The stimulation processor 118 converts stimulation data into stimulation signals that stimulate the electrodes 114 of the electrode array 112. The hermetically sealed case 120 is located within a processor portion 122 of the housing 102. A magnet apparatus 20 (or 20a-20f) is located within an antenna portion 124 of the housing 102. The magnet apparatus 20, which is used to maintain the position of a headpiece transmitter over the antenna 108, is centered relative to the antenna 108.

Figure 27:
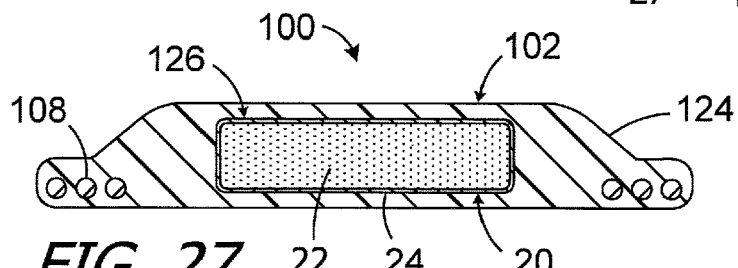
FIG. 27 is a section view taken along line 27-27 in FIG. 26.
Figure 28:
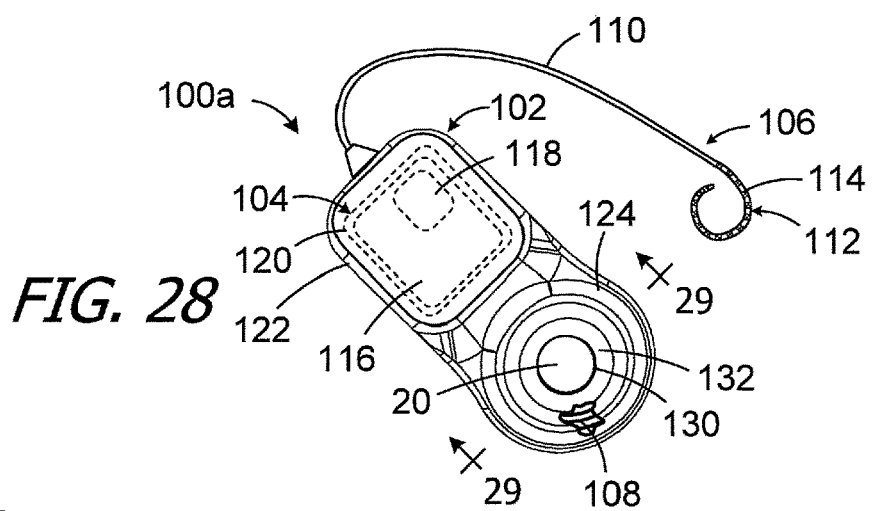
FIG. 28 is a plan view of a cochlear implant in accordance with one embodiment of a present invention.
Figure 29:
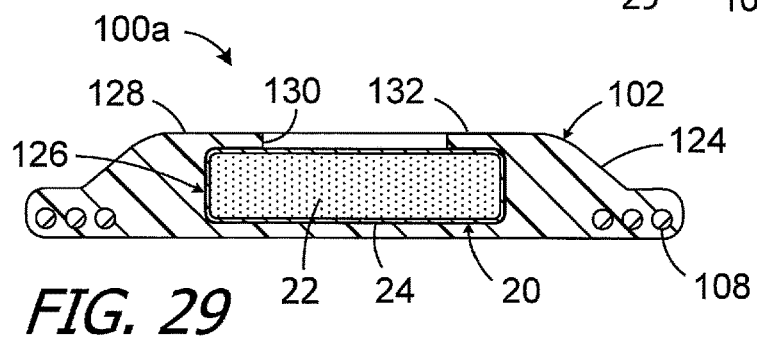
FIG. 29 is a section view taken along line 29-29 in FIG. 28.

Turning to FIG. 27, the exemplary housing antenna portion 124 includes a disk-shaped magnet pocket 126 in which the magnet apparatus 20 (or 20a-20f) is located. The magnet apparatus 20 is a permanent part of the cochlear implant 100 and is molded into the housing 102. The magnet apparatus may be removable in other implementations. To that end, the exemplary cochlear implant 100a illustrated in FIGS. 28 and 29 is substantially similar to cochlear implant 100 and similar elements are represented by similar reference numerals. Here, however, the top wall 128 includes a circular aperture 130 that allows the magnet apparatus 20 (or 20a-20f) be inserted into, and removed from, the magnet pocket 126. The diameter of the magnet apparatus 20 (or 20a-20f) is larger than that of the circular magnet aperture 130, and portions of the top wall 128 between the magnet aperture 130 and the side surface of the magnet apparatus form an annular retainer 132.

Figure 30:
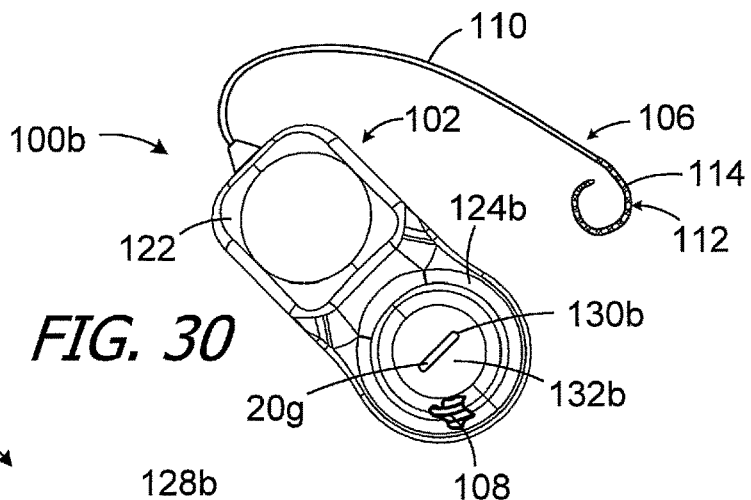
FIG. 30 is a plan view of a cochlear implant in accordance with one embodiment of a present invention.
Figure 31:
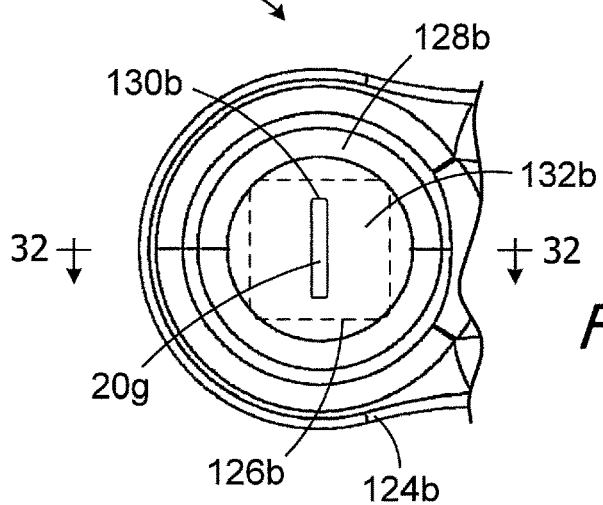
FIG. 31 is a plan view of a portion of the cochlear implant illustrated in FIG. 30.
Figure 32:
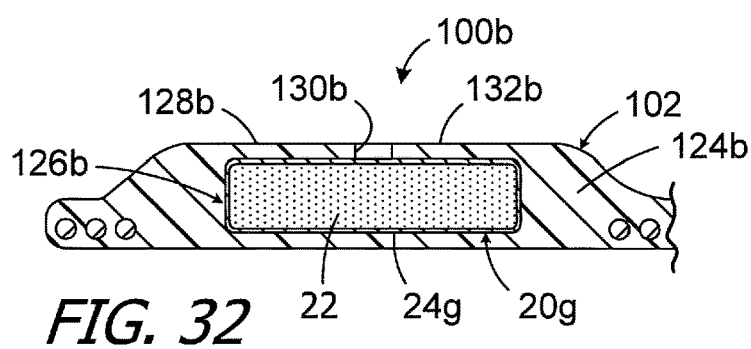
FIG. 32 is a section view taken along line 32-32 in FIG. 31.

Other cochlear implants may be configured for use with square magnet apparatus, such as those illustrated in FIGS. 20-25. To that end, the exemplary cochlear implant 100b illustrated in FIGS. 30-32 is substantially similar to cochlear implant 100 and similar elements are represented by similar reference numerals. Here, however, the antenna portion 124b includes a square magnet pocket 126b to accommodate the square magnet apparatus 20g and an elongate magnet slot (or "elongate slot") 130b, which extends from the housing exterior to the magnet pocket, in place of the circular magnet aperture. Although not so limited, the elongate slot 130b is rectangular in shape. The length of the elongate slot 130b may be at least 4 times greater than the width of the elongate slot and is 6.66 times greater in the illustrated embodiment. A retainer 132b is defined by portions of the top wall 128b between the magnet aperture 130b and the side surface of the magnet apparatus 20g.

Figure 34:
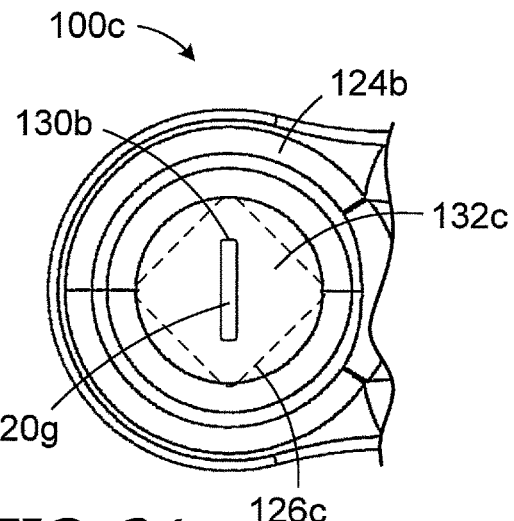
FIG. 34 is a plan view of a portion of a cochlear implant in accordance with one embodiment of a present invention.
Figure 35:
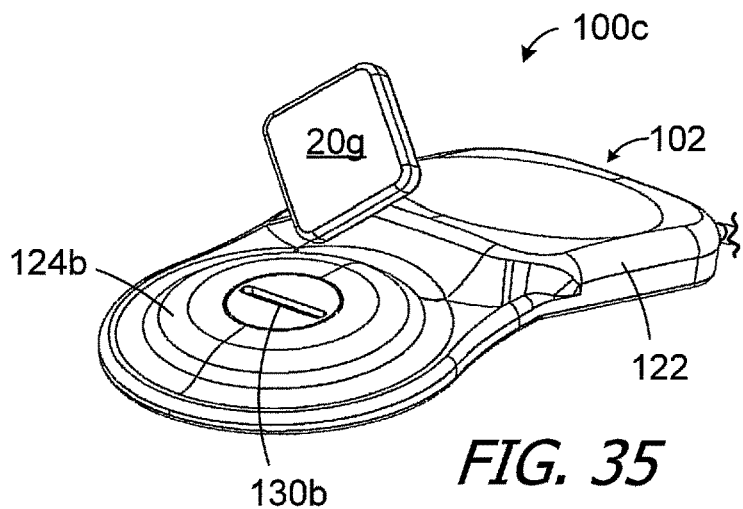
FIG. 35 is a perspective view showing a magnet being inserted into the cochlear implant illustrated in FIG. 34.
Figure 36:
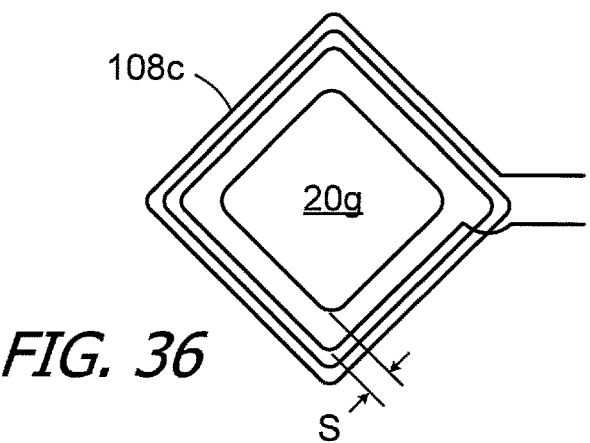
FIG. 36 is a plan view of a portion of the cochlear implant illustrated in FIG. 34.

It should also be noted here that although the cochlear implant 100b includes a generally circular coil antenna 108, other implementations may include a square antenna coil such as, for example, the square antenna discussed below with reference to FIGS. 34-36.

There are a number of advantages associated with the elongate slot 130b. By way of example, but not limitation, the open area of the elongate slot 130b is much less than the open area of a circular opening with a diameter that is equal to the length of the elongate slot. A larger portion of the top wall 128b forms the retainer 132b as compared to the portion of the top wall that forms an annular retainer when a circular opening is employed (see, e.g., annular retainer 132 in FIGS. 28-29), and the retainer 132b covers a larger portion of the top surface of the associated magnet apparatus as compared to an annular retainer. As a result, the retainer 132b is stronger than a comparable annual retainer, thereby reducing the likelihood that a magnet apparatus will rotate out of the magnet pocket when exposed to a strong magnetic field. The smaller open area associated with the elongate slot 130b also reduces the likelihood of biofilm formation as compared to larger circular openings.

Figure 33:
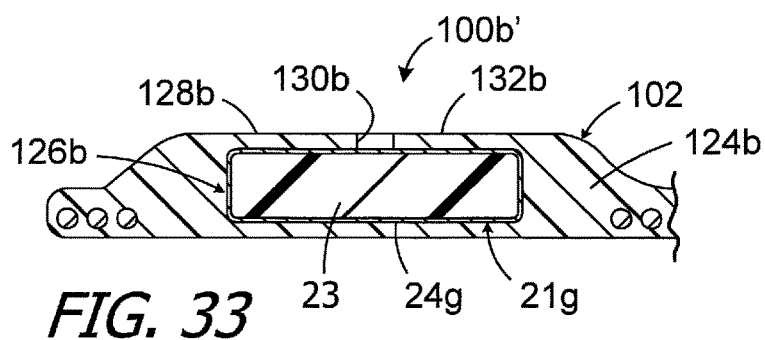
FIG. 33 is a section view of a portion of a cochlear implant in accordance with one embodiment of a present invention.

It should also be noted that cochlear implants with elongate magnet slots, including those described above with reference to FIGS. 30-32 and described below with reference to FIGS. 34-36, may include magnet apparatus other than those which include magnetic material particles and/or those with a square shape. To that end, and referring to FIG. 33, the exemplary cochlear implant 100b' is identical to cochlear implant 100b but for the magnet apparatus 21g, which includes a conventional solid magnet 23 within the square case 24g. In still other implementations, disk-shaped magnet apparatus, with either magnetic material particles or solid magnets, may be employed in cochlear implants that include a magnet slot.

The orientation of the square magnet pocket 126b is not limited to the orientation illustrated in FIG. 31, where two of the end walls of the pocket are parallel to the magnet slot 130b. For example, the exemplary cochlear implant 100c illustrated in FIGS. 34-36 is substantially similar to cochlear implant 100b and similar elements are represented by similar reference numerals. Here, however, one of the diagonals of the square magnet pocket 126c is perpendicular to the magnet slot 130b and the other diagonal is parallel. The retainer 132c has the same orientation as the magnet pocket 126c. The magnet apparatus 20g may be inserted through the slot 130b corner first (as shown in FIG. 35) to ease insertion as compared to, for example, a situation where the portion of the magnet apparatus initially passing through the slot was wider than the slot.

The exemplary cochlear implant 100c also includes an antenna 108c that has a square shape corresponding to that of the magnet apparatus 20g. The outer perimeter of the magnet apparatus 20g is separated from the antenna 108c by a space S. The antenna of the sound processor headpiece used in conjunction with the cochlear implant 100c (or other cochlear implant with a square antenna) may also have a square antenna and magnet.

Figure 37:
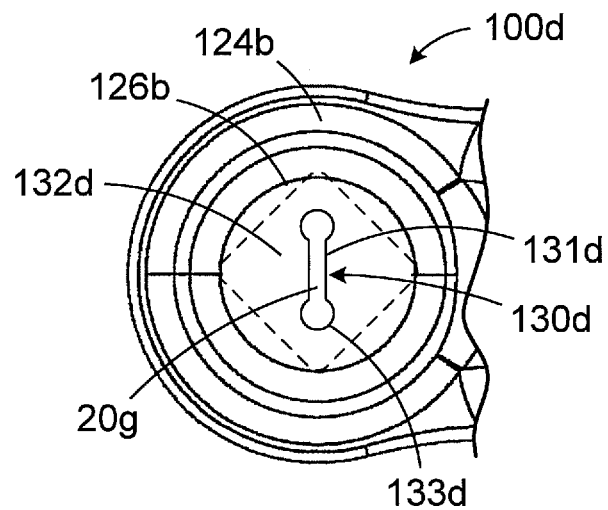
FIG. 37 is a plan view of a portion of a cochlear implant in accordance with one embodiment of a present invention.
Figure 38:
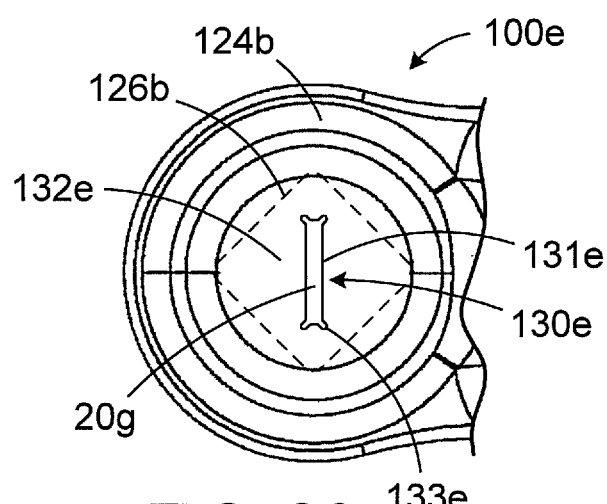
FIG. 38 is a plan view of a portion of a cochlear implant in accordance with one embodiment of a present invention.

Referring again to the elongate magnet slot, a wide variety of elongate slot shapes may also be employed. The exemplary magnet slot 130b is rectangular with rounded corners. In other implementations, the entire lateral ends may be semi-circular with diameters equal to the width of the magnet slot. Turning to FIG. 37, the elongate magnet slot 130d of the cochlear implant 100d (which is otherwise identical to cochlear implant 100c) includes a rectangular portion 131d and a circular portion 133d at each end of the rectangular portion whose diameters are greater than the width of the rectangular portion. A retainer 132d extends over the magnet pocket 126b. The circular portions 133d reduce the likelihood that the retainer 126d will tear as it is stretched during insertion of the magnet. Similarly, the elongate magnet slot 130e of the cochlear implant 100e illustrated in FIG. 38 (which is otherwise identical to cochlear implant 100b) includes a rectangular portion 131e and a pair of tabs 133e at both ends of the rectangular portion. A retainer 132e extends over the magnet pocket 126b. The tabs 133e reduce the likelihood that the retainer 126e will tear as it is stretched during insertion of the magnet.

Figure 39:
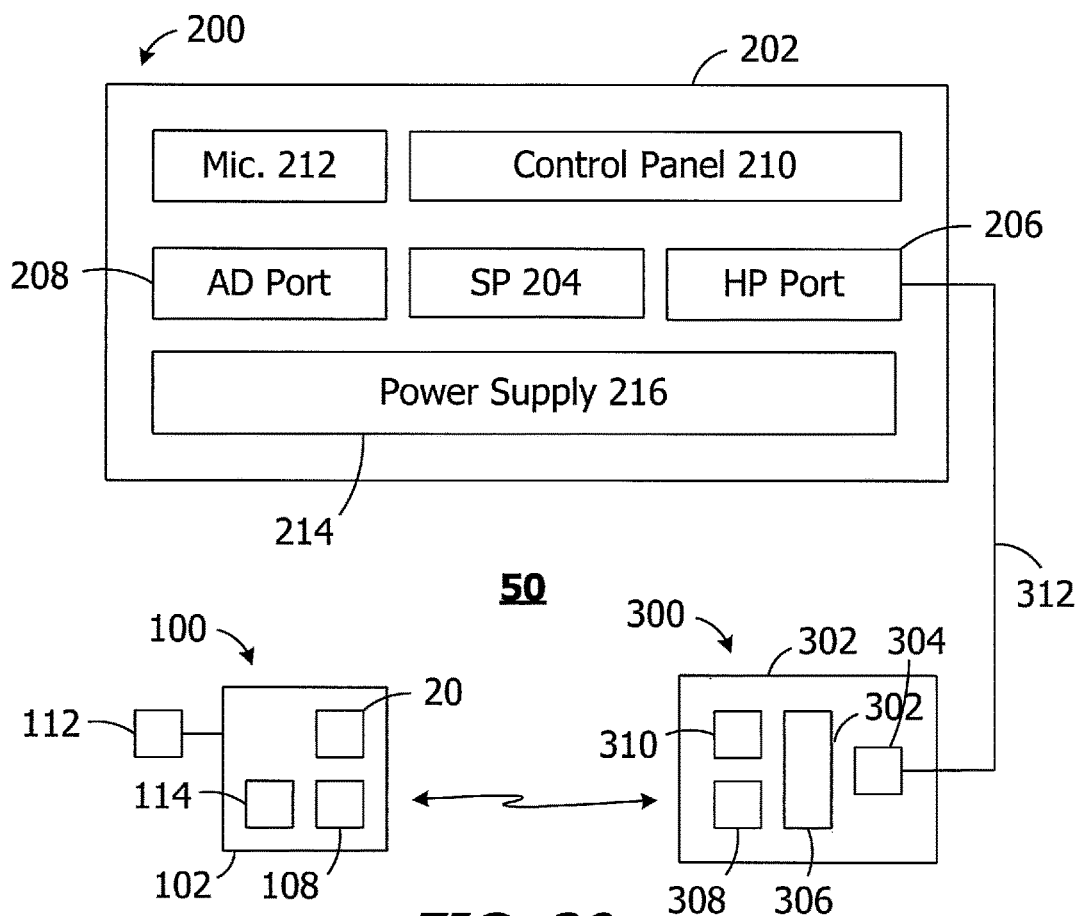
FIG. 39 is a block diagram of a cochlear implant system in accordance with one embodiment of a present invention.
Figure 40:
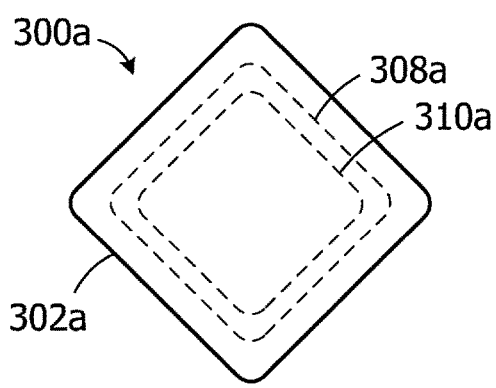
FIG. 40 is a plan view of a headpiece in accordance with one embodiment of a present invention

Turning to FIG. 39, the exemplary cochlear implant system 50 includes the cochlear implant 100 (or 100a-100e, a sound processor, such as the illustrated body worn sound processor 200 or a behind-the-ear sound processor, and a headpiece 300.

The exemplary body worn sound processor 200 in the exemplary ICS system 50 includes a housing 202 in which and/or on which various components are supported. Such components may include, but are not limited to, sound processor circuitry 204, a headpiece port 206, an auxiliary device port 208 for an auxiliary device such as a mobile phone or a music player, a control panel 210, one or microphones 212, and a power supply receptacle 214 for a removable battery or other removable power supply 216 (e.g., rechargeable and disposable batteries or other electrochemical cells). The sound processor circuitry 204 converts electrical signals from the microphone 212 into stimulation data. The exemplary headpiece 300 includes a housing 302 and various components, e.g., a RF connector 304, a microphone 306, an antenna (or other transmitter) 308 and a positioning magnet apparatus 310, that are carried by the housing. The magnet apparatus 310 may consist of a single magnet or, as is discussed below with reference to FIG. 41, may consist of one or more magnets and a shim. The headpiece 300 may be connected to the sound processor headpiece port 206 by a cable 312. The positioning magnet apparatus 310 is attracted to the magnet apparatus 20 of the cochlear implant 100, thereby aligning the antenna 308 with the antenna 108. The stimulation data and, in many instances power, is supplied to the headpiece 300. The headpiece 300 transcutaneously transmits the stimulation data (and in many instances power) to the cochlear implant 100 by way of a wireless link between the antennae. The stimulation processor 114a converts the stimulation data into stimulation signals that stimulate the electrodes 112a of the electrode array 112.

In at least some implementations, the cable 312 will be configured for forward telemetry and power signals at 49 MHz and back telemetry signals at 10.7 MHz. It should be noted that, in other implementations, communication between a sound processor and a headpiece and/or auxiliary device may be accomplished through wireless communication techniques. Additionally, given the presence of the microphone(s) 212 on the sound processor 200, the microphone 306 may be also be omitted in some instances. The functionality of the sound processor 200 and headpiece 300 may also be combined into a single head wearable sound processor. Examples of head wearable sound processors are illustrated and described in U.S. Pat. Nos. 8,811,643 and 8,983,102, which are incorporated herein by reference in their entirety.

The exemplary headpiece antenna may be configured to correspond to the shape of the cochlear implant antenna. The headpiece antenna may have a circular shape in those instances where the cochlear implant antenna is circular (e.g., the implant 100). Alternatively, and as illustrated for example in FIG. 40, the exemplary headpiece 300a includes an antenna 308a with a square shape. The headpiece magnet 310a also has a square shape, as does the housing 302a. The result is smaller headpiece (i.e., a headpiece that covers a smaller portion of the wearer's head) than a headpiece with a circular antenna and magnet. The headpiece 300a may be used in conjunction with, for example, the cochlear implants illustrated in FIGS. 34-38.

Figure 41:
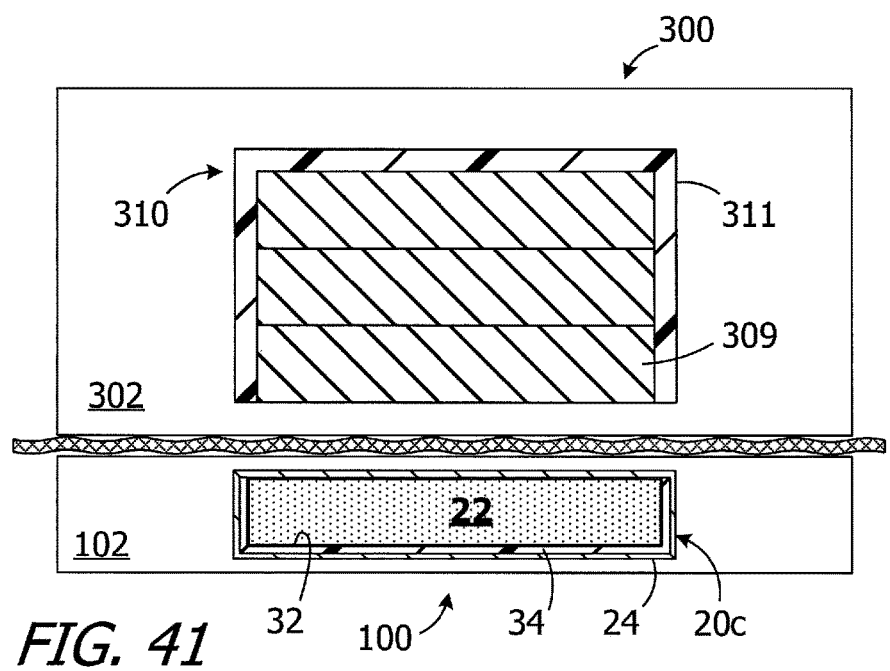
FIG. 41 is a section view showing portions of a system in accordance with one embodiment of a present invention.

Turning to FIG. 41, and as noted above, the respective configurations of the magnet apparatus 20c (or 20-20b and 20d-20h) in the cochlear implant 100 (or 100a-100e) and the magnet apparatus 308 in the headpiece 300 create a pull force there between that is about 2.2±0.1 N with a 3 mm air gap. The magnetic field generated by the magnet apparatuses 20-20d is weaker than a similarly sized conventional magnet apparatus that includes a solid block magnet in place of the magnetic material particles 22. The exemplary headpiece 300, on the other hand, has a magnet apparatus 308 that is configured to generate a stronger magnetic field than that associated with a conventional headpiece having a similar configuration. As a result, the present implant/headpiece system is able to provide the above-described benefits associated with the movable magnetic material particles without increasing the thickness of the implant magnet and, accordingly, the thickness of the implant itself, as compared of conventional implants. The elements of the implant 100 and the headpiece 300 that are not discussed in the context of FIG. 41 have been omitted from FIG. 41 for the sake of simplicity.

The exemplary magnet apparatus 308 illustrated in FIG. 41 includes a plurality of solid block magnets 309 and a shim 311. The strength of the magnetic field associated with the headpiece may be adjusted by replacing one or two of the magnets with a similarly sized plastic spacer. In other implementations, a single, thick magnet may be employed. The magnets 309 are disk-shaped in the illustrated embodiment, but other shapes may be employed. The shim 311 increases the flux density and focus the magnetic field associated with the magnets 309 toward the patient's skin and the internal magnet apparatus 20c. Although the present shims are not so limited, the exemplary shim 311 is cup-shaped and may be about 1.5 mm thick and formed from iron or mu-metal. In other implementations, a flat disk positioned above the magnets 309 may be employed.

By way of example, but not limitation, the following are specific examples of the magnet apparatus 308 that will, in combination with an implant 100 having the internal magnet apparatus 20c and isotropic neodymium particles 22 with a mesh size that ranges from 300 μm to 500 μm, provide a pull force of about 2.2±0.1 N when there is a spacing of about 3 mm between the external magnet apparatus 308 and the internal magnet apparatus 20c. A magnet apparatus 308 with the shim 311 and three N52 magnets that are 12.7 mm in diameter and 1.5 mm thick is one example. Another example is a magnet apparatus 308 with the shim 311 and a single N52 magnet that is 10.0 mm in diameter and 5.0 mm thick. In those instances where even more pull force is required, e.g., where a patient has a relatively thick skin flap, a magnet apparatus 308 with the shim 311 and a single N52 magnet that is 12.7 mm in diameter and 5.0 mm thick may be employed. It should also be noted that particles 22 having a mesh size that ranges from 100 μm to 300 μm may be used when the headpiece includes such a magnet apparatus. In another otherwise identical example, which instead employs anisotropic neodymium particles 22 with a mesh size that ranges from 50 μm to 200 μm, the pull force is about 2.4±0.1 N when there is a spacing of about 3 mm and the magnet apparatus 308 includes two N52 magnets that are 12.7 mm in diameter and 1.5 mm thick. The pull force at about 3 mm increases to about 3.0±0.1 N when a third N52 magnet (12.7 mm in diameter and 1.5 mm thick) is added to the magnet apparatus 308.

Although the inventions disclosed herein have been described in terms of the preferred embodiments above, numerous modifications and/or additions to the above-described preferred embodiments would be readily apparent to one skilled in the art. By way of example, but not limitation, the inventions include any combination of the elements from the various species and embodiments disclosed in the specification that are not already described. In some instances, a lubricant such as vegetable oil may be applied to the particles 22 to reduce friction and improvement movement of the particles relative to one another. It is intended that the scope of the present inventions extend to all such modifications and/or additions and that the scope of the present inventions is limited solely by the claims set forth below.

We claim:

1. A cochlear implant, comprising:
a cochlear lead including a plurality of electrodes;
an antenna;
a stimulation processor operably connected to the antenna and to the cochlear lead; and
a magnet apparatus, associated with the antenna, including a case with an internal volume, a divider that separates the internal volume into a plurality of sub-volumes, and respective pluralities of magnetic material particles packed within the sub-volumes in such a manner that adjacent magnetic material particles are in contact with one another and are also movable relative to one another.

2. A cochlear implant as claimed in claim 1, wherein the magnetic material particles are each are free to move from one X-Y-Z coordinate to another and to rotate in any direction.

3. A cochlear implant as claimed in claim 1, wherein the magnetic material particles are at least substantially polyhedral in shape; and/or
the magnetic material particles define mesh sizes that range from 50 μm to 500 μm, or from 100 μm to 300 μm, or from 300 μm to 500 μm; and/or
the magnetic material particles are formed from a material selected from the group consisting of neodymium-iron-boron, magnetic material, isotropic neodymium, anisotropic neodymium, samarium-cobalt.

4. A cochlear implant as claimed in claim 1, wherein the case comprises a disk-shaped case or a square case.

5. A cochlear implant as claimed in claim 1, wherein the case is formed from a material selected from the group consisting of paramagnetic metal and plastic.

6. A cochlear implant as claimed in claim 1, further comprising:
a magnetic field focusing shim located within the case.

7. A cochlear implant as claimed in claim 1, wherein the antenna, the stimulation processor and the magnet apparatus are located within a flexible housing.

8. A cochlear implant as claimed in claim 1, wherein at least some of the plurality of sub-volumes are three-dimensionally uniform.

9. A cochlear implant as claimed in claim 8, wherein at least some of the plurality of sub-volumes are at least substantially three-dimensionally uniform.

10. A cochlear implant as claimed in claim 1, wherein at least some of the plurality of sub-volumes are at least substantially three-dimensionally uniform.

11. A cochlear implant as claimed in claim 1, wherein
the case includes a base and a cover, the base defines a height, the divider defines a height, and the base height is 90% to 99% of the divider height.

12. A cochlear stimulation system, comprising:
a cochlear implant as claimed in claim 1; and
a sound processor including
   a housing,
   sound processor circuitry carried within the housing, and
   a communication device adapted to operably connect the sound processor circuitry to the cochlear implant.

13. A cochlear stimulation system as claimed in claim 12, wherein
the communication device comprises a square antenna.

14. A cochlear stimulation system as claimed in claim 13, wherein
the sound processor includes a headpiece and the square antenna part of the headpiece.

15. A cochlear stimulation system as claimed in claim 14, wherein
the headpiece includes a square housing.

\* \* \* \* \*

UNITED STATES PATENT AND TRADEMARK OFFICE
CERTIFICATE OF CORRECTION

PATENT NO. : 10,300,276 B2
APPLICATION NO. : 15/568470
DATED : May 28, 2019
INVENTOR(S) : Sung Jin Lee et al.

It is certified that error appears in the above-identified patent and that said Letters Patent is hereby corrected as shown below:

On the Title Page

Item (71) Applicants, delete "; James George Elcoate Smith, Santa Clarita, CA (US)"

Signed and Sealed this
Second Day of July, 2019

Andrei Iancu
*Director of the United States Patent and Trademark Office*